United States Patent
Nishiyama et al.

(10) Patent No.: US 7,359,044 B2
(45) Date of Patent: Apr. 15, 2008

(54) METHOD AND APPARATUS FOR INSPECTING PATTERN DEFECTS

(75) Inventors: Hidetoshi Nishiyama, Fujisawa (JP); Yukihiro Shibata, Fujisawa (JP); Shunji Maeda, Yokohama (JP); Minoru Yoshida, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 305 days.

(21) Appl. No.: 11/180,536

(22) Filed: Jul. 14, 2005

(65) Prior Publication Data

US 2006/0012780 A1    Jan. 19, 2006

(30) Foreign Application Priority Data

Jul. 14, 2004    (JP) ............................. 2004-206688

(51) Int. Cl.
*G01N 21/00* (2006.01)

(52) U.S. Cl. ................. 356/237.4; 356/237.2; 356/237.5; 356/328; 250/559.4

(58) Field of Classification Search ................ 356/204, 356/205, 37.2–237.52; 250/559.4–559.45
See application file for complete search history.

(56) References Cited

U.S. PATENT DOCUMENTS

| | | | |
|---|---|---|---|
| 5,936,726 A * | 8/1999 | Takeda et al. ............ | 356/237.2 |
| 6,411,377 B1 * | 6/2002 | Noguchi et al. ......... | 356/237.4 |
| 6,825,930 B2 * | 11/2004 | Cronin et al. .............. | 356/328 |
| 2005/0110988 A1 * | 5/2005 | Nishiyama et al. ...... | 356/237.5 |

FOREIGN PATENT DOCUMENTS

| | | |
|---|---|---|
| JP | 61-212708 | 9/1986 |
| JP | 07-318326 | 12/1995 |
| JP | 08-320294 | 12/1996 |
| JP | 10-078668 | 3/1998 |
| JP | 2000-155099 | 6/2000 |
| JP | 2001-194323 | 7/2001 |
| JP | 2002-277404 | 9/2002 |
| JP | 2003-130808 | 5/2003 |

* cited by examiner

*Primary Examiner*—Layla G. Lauchman
*Assistant Examiner*—Iyabo S Alli
(74) *Attorney, Agent, or Firm*—Antonelli, Terry, Stout & Kraus, LLP.

(57) ABSTRACT

A method of inspecting pattern defects can detect target defects in various processes stably by reducing erroneous detection of grains and morphology and decreasing the influence of an intensity nonuniformity in interference light. For this purpose, lights emitted from two sources of illumination capable of outputting a plurality of wavelengths are reflected by a beam splitter and irradiated onto a wafer. Diffracted light from the wafer is converged by an objective lens, is made to pass through light modulation units and imaged on an image sensor in a light detection unit. Then, defects are detected in a signal processing unit. Further, the optical modulation unit is made to have a structure that uses a plurality of optical components selectively and which can be optimized according to target defects.

23 Claims, 12 Drawing Sheets

FIG.15

```
Inspection image        Reference image
         │                     │
         ▼                     ▼
    ┌─────────────────────────────┐
    │      Noise reduction        │──S1901
    └─────────────────────────────┘
                  │
    ┌─────────────────────────────┐
    │     Image construction      │──S1902
    └─────────────────────────────┘
                  │
    ┌─────────────────────────────┐
    │ Calculation of feature quantity of image │──S1903
    └─────────────────────────────┘
                  │
    ┌─────────────────────────────┐
    │  Comparison of feature quantity  │──S1904
    └─────────────────────────────┘
                  │
    ┌─────────────────────────────┐
    │      Mergence of images     │──S1905
    └─────────────────────────────┘
                  │
    ┌─────────────────────────────┐
    │ Defect detection and determination │──S1906
    └─────────────────────────────┘
```

FIG.16

| | | | | |
|---|---|---|---|---|
| Name of kind | | | | 2101 |
| Process name | | | | 2102 |
| Watched area data | | | | 2103 |
| Process rule | 2104 | | | 2105 |
| Inspection layer information | Resist | ● For KrF | ○ For ArF | ○ Other |
| | After deposition (without CMP) | ○ Insulator film | ○ Metal film | ○ Other |
| | After CMP | ○ STI | ○ Insulator film deposition | ○ Metal film deposition (other than CU) |
| | | ○ After filling up hole | ○ Cu damascene | ○ Other |
| | After etching | ○ Ploy-Si (gete) | ○ Insulator film | |
| | | ○ Metal film | ○ Other | |

FIG.17

| | | Illumination wavelength | Aperture diapghragm | light modulation condition | | |
|---|---|---|---|---|---|---|
| | | | | A | B | C |
| Resist | For KrF | $\lambda 1$ | F2 | A2 | B1 | C2 |
| | For ArF | $\lambda 2$ | F2 | A2 | B1 | C3 |
| | Other | $\lambda 1 + \lambda 2$ | F2 | A2 | B1 | C2 |
| After deposition (without CMP) | Insulator film | $\lambda 1 + \lambda 2$ | F3 | A3 | B2 | C1 |
| | Metal film | $\lambda 1 + \lambda 2$ | F3 | A1 | B2 | C2 |
| | Other | $\lambda 1 + \lambda 2$ | F1 | A1 | B2 | C1 |
| After CMP | STI | $\lambda 2$ | F1 | A3 | B2 | C1 |
| | Insulator film deposition | $\lambda 1 + \lambda 2$ | F1 | A3 | B2 | C1 |
| | Metal film deposition (other than CU) | $\lambda 2$ | F1 | A1 | B2 | C2 |
| | After filling up hole | $\lambda 1 + \lambda 2$ | F1 | A1 | B2 | C1 |
| | Cu damascene | $\lambda 1 + \lambda 2$ | F1 | A1 | B2 | C1 |
| | Other | $\lambda 1 + \lambda 2$ | F1 | A1 | B2 | C1 |
| After etching | Ploy-Si (gete) | $\lambda 1$ | F2 | A2 | B1 | C2 |
| | Insulator film | $\lambda 1 + \lambda 2$ | F2 | A3 | B1 | C2 |
| | Metal film | $\lambda 1 + \lambda 2$ | F3 | A2 | B1 | C4 |
| | Other | $\lambda 1 + \lambda 2$ | F1 | A2 | B1 | C2 |

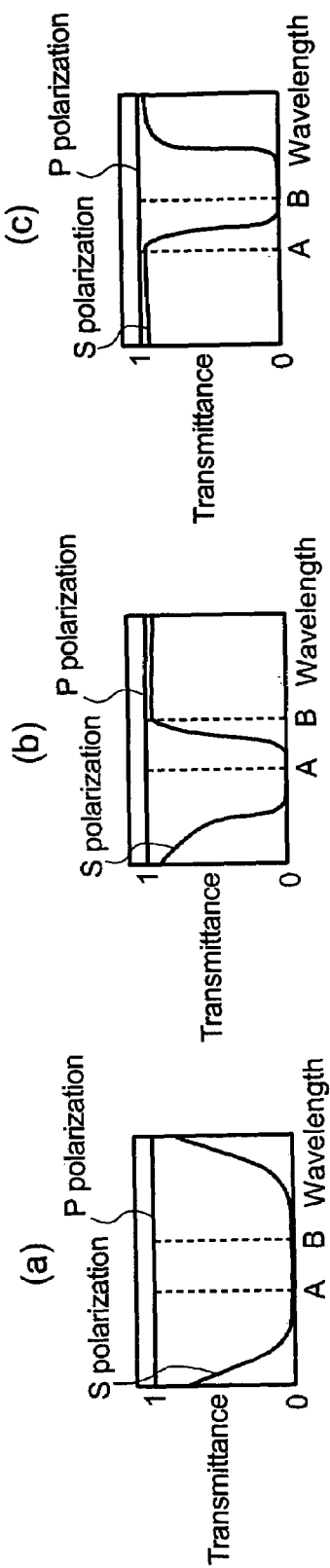
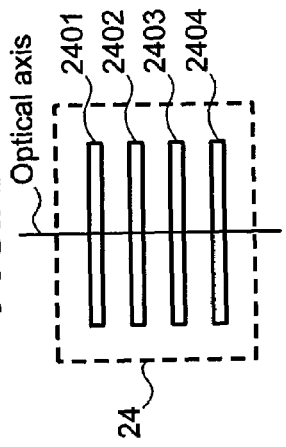
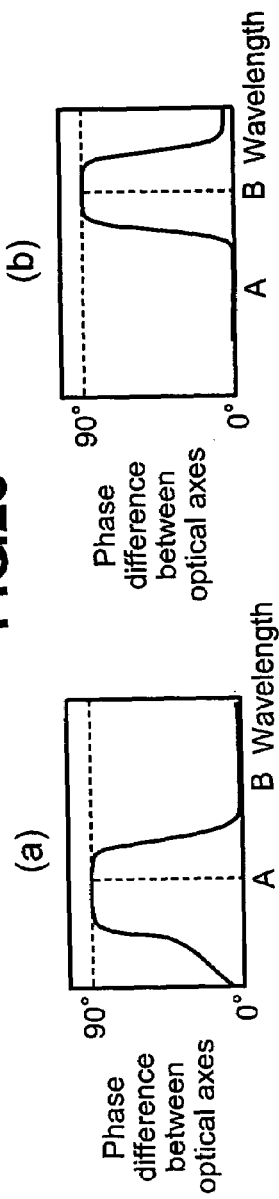
FIG.21
FIG.22
FIG.23

METHOD AND APPARATUS FOR INSPECTING PATTERN DEFECTS

BACKGROUND OF THE INVENTION

The present invention relates in general to pattern defect inspection and foreign material inspection for detecting defects (short circuits, breaking of wire, etc.) in a circuit pattern and foreign materials on a sample; and, more particularly, the invention relates to a method and apparatus for inspecting for defects and foreign materials on a circuit pattern, such as those which appear in semiconductor wafers, liquid crystal displays, photomasks, etc. In the following description, a defect includes the presence of foreign material.

Conventionally, as an example of an inspection apparatus of this kind, there is a technology in which an image of a sample is picked up using an imager, such as an image sensor, while the sample is being moved, and gray scales of the detected image signal and of an image signal that has been delayed for a fixed time are compared, whereby a portion where the two signals do not coincide is identified as a defect (JP-A No. 212708/S61).

Moreover, as another example of technology that is related to defect inspection of a sample, there is a technique for performing high-accuracy inspection on a semiconductor wafer, such that an area of high pattern density, such as a memory mat part, and an area of low pattern density, such as a peripheral circuit, are mixed within the same die (JP-A No. 320294/1996).

Furthermore, as a way of detecting an ultra-fine circuit pattern, there is a technique for detecting the circuit pattern with high resolution, while illumination light or its diffracted light is controlled optically (JP-A No. 318326/1997 and JP-A No. 155099/2000).

In addition, among techniques for inspecting the circuit pattern of a photomask, there is a method in which UV (Ultra Violet) laser light, such as that of an excimer laser, is used as a light source, its coherence is reduced by rotating a diffuser inserted in the light path and irradiated onto a mask for uniform illumination, and the quality of the photomask is determined by calculating feature quantities from obtained image data of the mask (JP-A No. 78668/1998).

Moreover, as an example of inspection using laser light in the range of UV to DUV (Deep UV), there is a method of reducing a laser's coherence by swinging the laser light (JP-A No. 194323/2001).

In the LSI manufacture of recent years, the pattern width formed on a wafer has been reduced to 200 nm or less because of miniaturization of the circuit pattern in response to a demand for high integration, and, accordingly, the dimensions of defects to be detected also have become ultra-fine. In particular, defects have been reported that are difficult for the conventional technology to detect, such as those referred to as "Non Visual Defects."

Under such circumstances, technologies for realizing a higher NA (Numerical Aperture) in an objective lens to be used for inspection and super resolution are being developed. Since making the NA of the objective lens for inspection higher has already reached the physical limit, it is an essential approach to make the wavelength of illumination light used for detection shorter, i.e., toward the areas of UV (Ultra Violet) light and DUV (Deep UV) light.

LSI devices are becoming complicated and diversified in connection with the structures of inspection target patterns, such as in memory products formed mainly with repeating patterns and in logic products formed mainly with non-repeating patterns, and, consequently, it has become difficult to find with certainty target defects that require product control at the time of the manufacture of LSI devices. FIG. 2 shows an example of various target defects. Target defects that are desired to be detected are voids and scratches produced in a CMP process, in addition to the presence of foreign materials and pattern defects produced in each process. Moreover, there are short circuits and bridges in gate wiring in metal wiring parts, such as parts made of aluminum (Al), as well as non-conduction and non-aperture conditions of contact holes connecting the wiring.

Because underlayer patterns at locations where defects have occurred have become diversified, and due to the fact that the shape of a defect itself has been minimized (to dimensions equal to or less than the resolution of the conventional optical system) and diversified, it is difficult to detect many defects. Here, as factors that impede detection of target defects, there are grains produced in the metal-wiring processes, such as grains of Al, and a minute unevenness called a morphology. Moreover, in a process where a transparent film (here, meaning transparent to the illumination light), such as insulator film, is exposed at the outermost surface, an intensity nonuniformity in interference light due to minute film thickness differences of the transparent film appear as optical noise. Therefore, there is a problem in that target defects whose dimensions are equal to or less than the resolution of the optical system are made apparent, while erroneous detection of a grain and morphology is lessened, and the influence of the intensity nonuniformity in interference light is reduced.

There is a method of reducing the above-mentioned intensity nonuniformity in interference light by using lamps as a light source, for which light of a plurality of wavelengths is irradiated. However, if the light of a plurality of wavelengths is obtained from one light source, the ratio of wavelength intensities changes in accordance with the time of use of the lamp. FIG. 3 is a graph showing the output intensity of a certain lamp over time. FIG. 3 shows the output intensity 51 of a wavelength $\lambda_1$ and the output intensity 52 of another wavelength $\lambda_2$. At time A, the intensity ratio of the output intensity 51 to the output intensity 52 is about 3, but at time B the intensity ratio becomes 7.5. This is because the attenuation rate over time of use is different for each wavelength. If the intensity ratio is changed in this way, the detected optical image will change in each measurement; therefore, there is a problem in that defect detection cannot be carried out stably.

SUMMARY OF THE INVENTION

It is an object of the present invention to provide a method and apparatus capable of successfully detecting target defects in various processes by reducing erroneous detection of grains and morphology and by decreasing the influence of the intensity nonuniformity in interference light.

That is, in accordance with this invention, a pattern inspection apparatus for inspecting defects of a pattern formed on a sample is provided with: illumination means for illuminating a sample on whose surface the pattern was formed; imaging optical system means for forming an optical image of the pattern of the sample illuminated by this illumination means; detecting means for detecting an image of the pattern of the sample by detecting the optical image that is formed by this imaging optical system means; defect detecting means for detecting defects of the pattern on the sample by processing the image detected by this detecting means; and selecting means for selecting a combination of an illumination wavelength of the illumination means and an aperture diaphragm of the illuminating means and/or the imaging optical system means according to the pattern; wherein, when the sample is illuminated by light emitted from the illumination means, the optical image of the pattern of the illuminated sample is formed by the imaging optical system, the image of the pattern of the sample is detected by detecting this formed optical image, and defects of the pattern on the sample are detected by processing this detected image. The pattern inspection apparatus for inspecting defects of the pattern is modified such that the optical image of the pattern of the sample is formed by selecting a combination of a wavelength of light illuminating the sample and the aperture diaphragm of the illumination means and/or the imaging optical system means according to the pattern formed on the sample surface.

Moreover, according to this invention, the pattern defect inspection apparatus comprises: illumination means for illuminating a sample on whose surface a pattern was formed; imaging optical system means for forming an image of diffracted light from the sample illuminated by this illumination means; light modulating means, being disposed in an optical path of this illumination means and/or imaging optical system means, for controlling the intensity and/or phase of the light; image detecting means for picking up a formed image of diffracted light from the sample by the imaging optical system means and outputting an image signal representative thereof; and defect detecting means for detecting defects of the pattern formed on the sample by processing the image signal outputted from this image detecting means; wherein, when the sample on whose surface a pattern was formed is illuminated by light emitted from the illumination means, an optical image of the pattern of the sample thus illuminated is formed by the imaging optical system, an image of the pattern of the sample is detected by detecting this formed optical image, and defects of the pattern on the sample are detected by processing this detected image. The pattern defect inspection apparatus is disposed in the optical path of the illumination means and/or imaging optical system, and it is configured to control the intensity and/or phase of the light.

According to this invention, it becomes possible to reduce erroneous detection of grains and morphology, the decrease the influence of an intensity nonuniformity in interference light, and, thereby, to detect various defects on the wafer stably. These and other objects, features and advantages of the invention will be apparent from the following more particular description of preferred embodiments of the invention, as illustrated in the accompanying drawings.

BRIEF DESCRIPTION OF THE DRAWINGS

FIG. 10(a) shows a case in which the directions of the optic axes relative to the optical axis are the same. FIG. 10(b) shows a case in which the directions of the optic axes relative to the optical axis are different from each other.

FIG. 15 is a flowchart showing the flow of signal processing.

FIG. 16 is a diagram of a screen used to set up conditions.

FIG. 17 is a table showing a relationship between inspection target layers of a device and alterable optical conditions in an inspection apparatus for each production process.

FIG. 21(a) is a graph showing a characteristic of a PBS used in the first embodiment.

FIG. 21(b) is a graph showing a characteristic of a PBS used in the second embodiment.

FIG. 21(c) is a graph showing a characteristic of a PBS used in the second embodiment, with reference to an example in which a transmittance characteristic to polarized light is different from the case shown in FIG. 21(b).

FIG. 22 is a diagram showing an example of a light modulation unit used in the second embodiment.

FIG. 23(a) is a graph showing a characteristic of a half wave plate 2401 of the light modulation unit used in the second embodiment.

FIG. 23(b) is a graph showing a characteristic of a half wave plate 2403.

DESCRIPTION OF THE PREFERRED EMBODIMENTS

Hereafter, various embodiments of the present invention will be described with reference to the drawings.

First Embodiment

Figure 1:
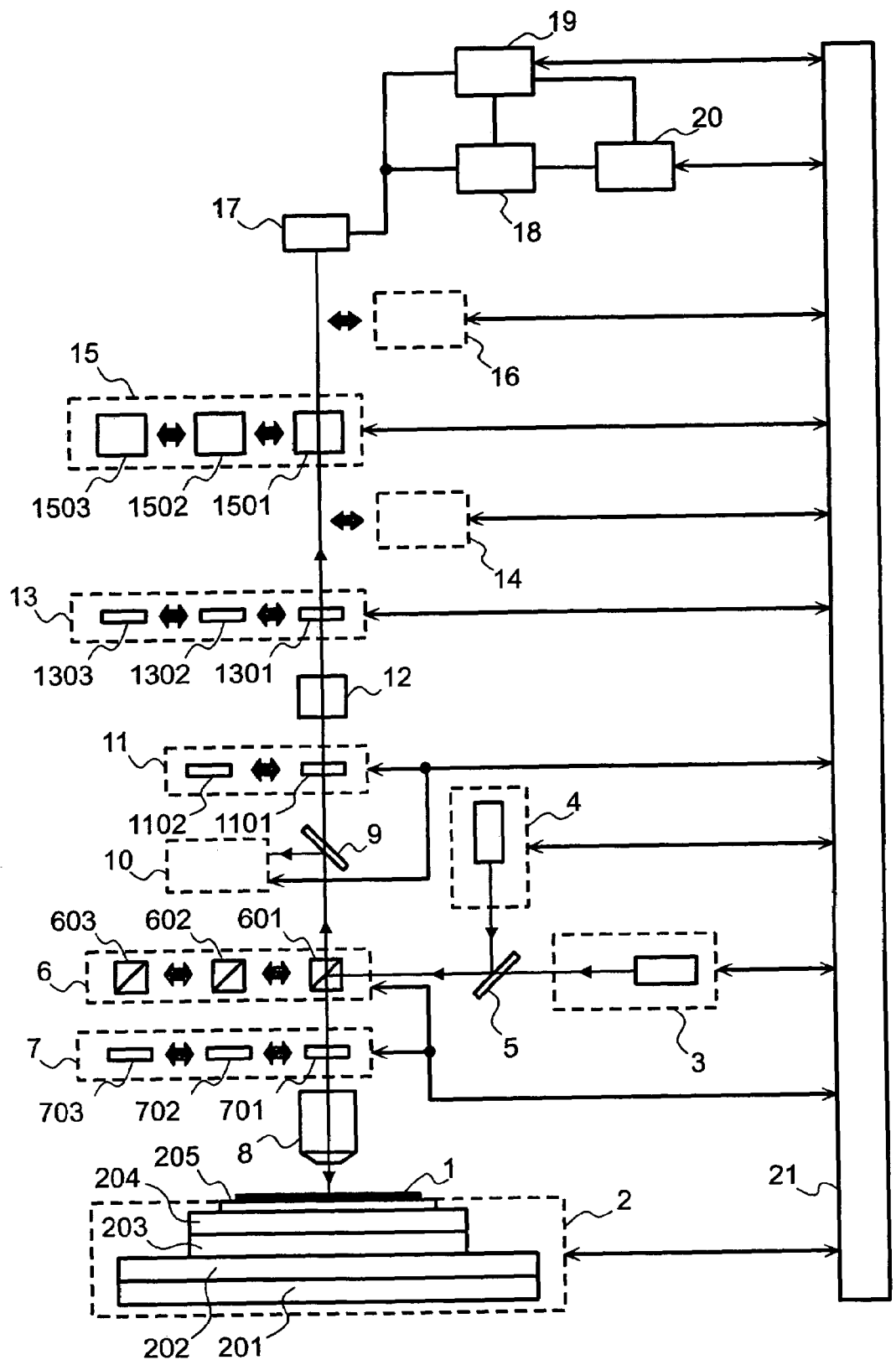
FIG. 1 is a diagram showing an outline of the structure of a first embodiment of an apparatus for inspecting pattern defects in accordance with the present invention.
Figure 2:
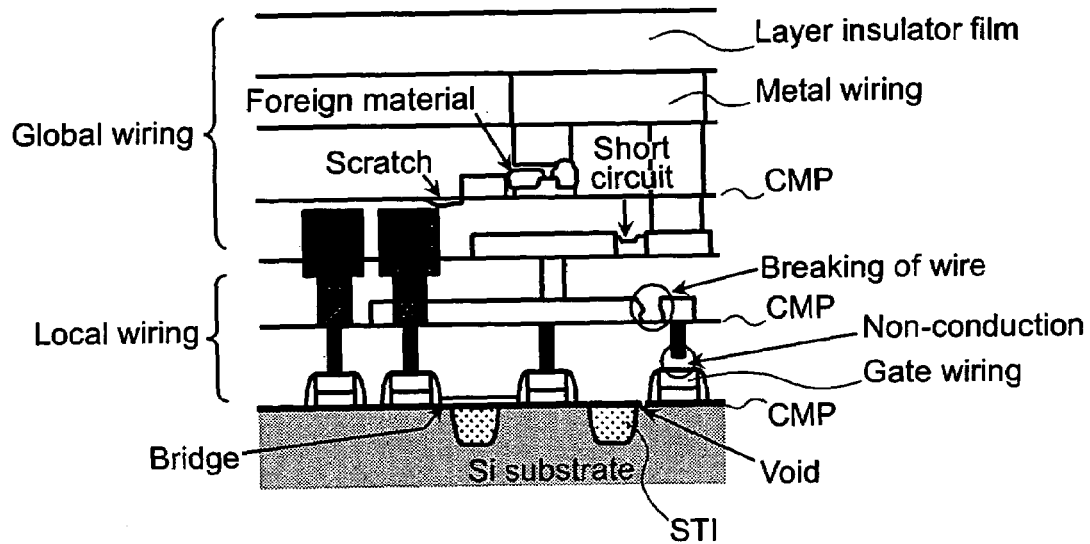
FIG. 2 is a diagram showing cross-sectional structure of an LSI having a variety of defects therein.
Figure 3:
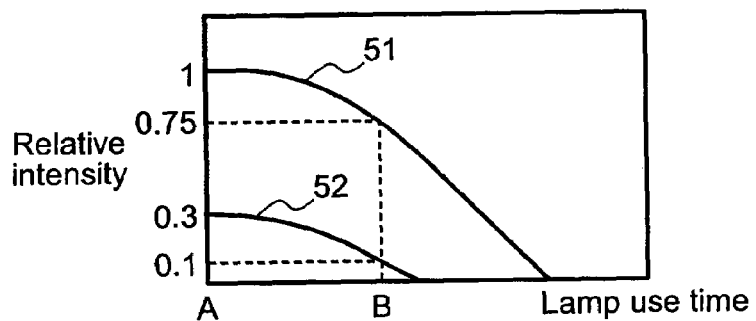
FIG. 3 is a graph showing a relationship between output intensity versus use time of a lamp light source.

An embodiment in which an inspection apparatus according to this invention is applied to the inspection of a semiconductor device is shown in FIG. 1. The pattern defect inspection apparatus of this invention is composed of a conveyance system 2 for supporting and moving a wafer 1 that represents a target of inspection, illumination means 3 and 4 having different wavelengths, a dichroic mirror 5, a beam splitter (hereinafter referred to as BS) unit 6, a light modulation A unit 7, an objective lens 8, a BS for A/F 9, A/F detection unit 10, a light modulation B unit 11, a relay lens 12, a light modulation C unit 13, a pupil observation unit 14, an imaging lens unit 15, a sample surface observation unit 16, a light detector unit 17, a signal processing circuit 18, an auto classification (hereinafter referred to as ADC) unit 19, an input/output part 20, a controller 21 for these units, and an unillustrated relay lens and mirror. Here, arrows connecting the controller 21 and the various units indicate communication of control signals, etc.

Next, the operations of the inspection apparatus will be explained. The optical axes of the illumination lights emitted from the illumination means 3 and 4 are brought in line by the dichroic mirror 5 and are made to enter the BS unit 6. A beam reflected by the BS unit 6 passes through the objective lens 8 via the light modulation A unit 7, and it is irradiated onto the wafer 1.

Light reflected by the wafer 1 passes through the BS unit 6 via the objective lens 8 and the light modulation A unit 7, and it is branched by the BS for A/F 9. The light, having passed through the BS for A/F 9, passes through the light modulation B unit 11, and it is converged by the relay lens 12 onto the light modulation C unit 13. This light modulation C unit 13 is disposed in a conjugate position relative to the pupil of the objective lens 8. The light, having passed through the light modulation C unit 13, passes through the imaging lens unit 15 to form an image onto an image sensor installed in the light detector unit 17, and it is converted into an image signal. The converted image signal is subjected to defect detection processing in the signal processing circuit 18, which detects defects on the wafer 1, and inspection results are displayed on the input/output part 20. The image signal and the signal subjected to the defect detection processing are also sent to the ADC unit 19, where they are subjected to ADC processing. The above-described operation is conducted while the wafer 1 is being moved by the conveyance system 2 to achieve inspection on the whole area of the wafer 1.

Incidentally, the input/output part 20 functions as an interface for receiving input information from the user, and it can transmit and receive a control signal to/from the controller 21. Moreover, the A/F detection unit 10 emits a signal for moving the wafer 1 to an object-side focal point position of the objective lens 8, and it adjusts the surface of the wafer 1 to the object-side focal point position of the objective lens 8 in real time by driving the conveyance system 2 via the controller 21. Furthermore, the pupil observation unit 14 has a function of observing a pupil part of the objective lens 8 by moving itself in and out of the optical axis area. The sample surface observation unit 16 has a function of observing the wafer 1 by moving itself in and out of the optical axis area.

Details of each part will be described below.

First, details of the conveyance system 2 will be described. The conveyance system 2 is composed of an X-axis stage 201, a Y-axis stage 202, a Z-axis stage 203, a θ-axis stage 204, and a wafer chuck 205. The X-axis stage 201 is capable of constant speed travel, and the Y-axis stage has a structure enabling stepwise travel. By using the X-axis stage 201 and the Y-axis stage 202, all locations in the wafer 1 can be moved to a position just under the center of the objective lens 8. Moreover, the Z-axis stage 203 has a function of elevating the wafer chuck 205 vertically; and, the θ-axis stage 204 rotates the wafer chuck 205 so that traveling directions of the X-axis stage 201 and the Y-axis stage 202 are aligned to a rotational direction of the wafer 1. Furthermore, the wafer chuck 205 has a function of fixing the wafer 1 by holding the wafer 1 by means of vacuum etc.

The illumination means 3 and 4 form beams that are irradiated onto the wafer 1. As the illumination light source, a laser light source and a lamp light source are used.

For the laser light source, visible light, ultraviolet light (hereinafter referred to as UV light), deep ultraviolet light (hereinafter referred to as DUV light), vacuum ultraviolet light, extreme ultra violet light, etc. are usable; and, as for a laser oscillation scheme, both continuous oscillation and pulsed oscillation may be used. It is preferable that the wavelength is roughly 550 nm or less, and, for example, sources of 532 nm, 355 nm, 266 nm, 248 nm, 200 nm, 193 nm, 157 nm, and 13 nm can be applied.

For the laser light source, a second harmonic (SHG), a third harmonic (THG), and a fourth harmonic (FHG) of the solid-state YAG laser (fundamental wave, wavelength 1024 nm) obtained by wavelength conversion with a nonlinear optical crystal, an excimer laser, and an ion laser may be used. Moreover, two different wavelengths may be resonated to oscillate another wavelength. This method consists of outputting a laser light having a wavelength of 199 nm by generating a sum frequency of an SHG wave (wavelength 488 nm) of Ar laser light and a YAG laser light having a wavelength of 1064 nm, and establishing resonance of it. As for a type of pulsed oscillation laser, a low frequency pulsed oscillation laser whose oscillation frequency is a few Hz, and a quasicontinuous oscillation pulsed laser of a few tens of MHz may be used. Furthermore, regarding a method of pulsed oscillation, both a Q-switch type and a mode-locked type may be used.

An advantage of each light source is that, if a light source having a short wavelength is used, the resolution of the optical system is improved and a high-sensitivity inspection can be expected. Moreover, since solid-state YAG lasers etc. do not need large-scale incidental facilities, an apparatus can be made small in scale and cheap. Moreover, if a pulsed oscillation laser having a high frequency is used, it can be handled equally with a high-output continuous oscillation laser. Therefore, it becomes possible to use cheap optical components with low transmittance or low reflectance, and an inexpensive apparatus can be realized.

Lamp light sources that emit in a wavelength band that is almost equivalent to those of the laser light sources can be used. For a lamp light source, a Xe lamp, a Hg—Xe lamp, a Hg lamp, a high pressure Hg lamp, an extra-high pressure Hg lamp, an electron-beam-gas-emission-lamp (output wavelengths are, for example, 351 nm, 248 nm, 193 nm, 172 nm, 157 nm, 147 nm, 126 nm, and 121 nm), etc. can be used, and what is necessary is just to be able to output a desired wavelength. Regarding a lamp selection method, any lamp of a desired wavelength and with high output may be selected, and it is preferable when the arc length of the lamp is short. This is because the choices of beam formation methods can be increased in number.

Hereafter, the illumination means using a laser light source will be explained with reference to FIGS. 4 to 7.

Figure 4:
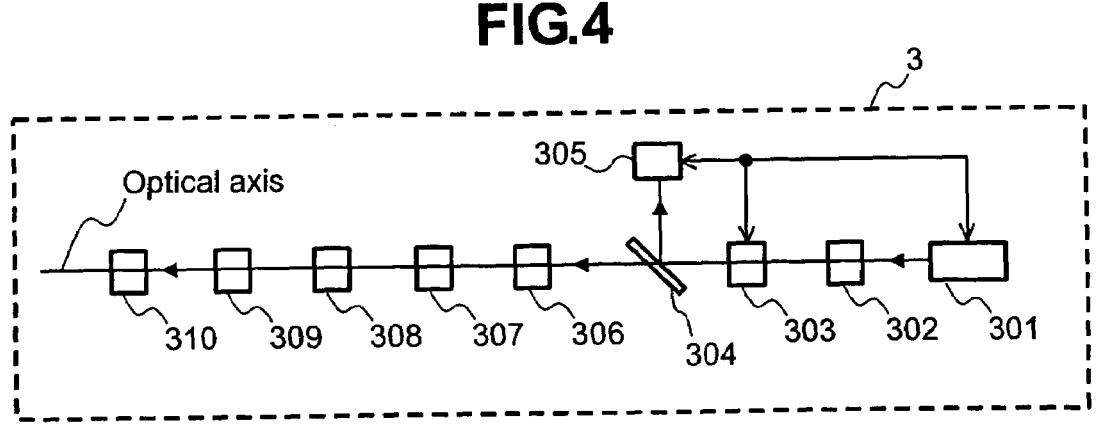
FIG. 4 is a diagram showing the structure of laser illumination means.
Figure 5:
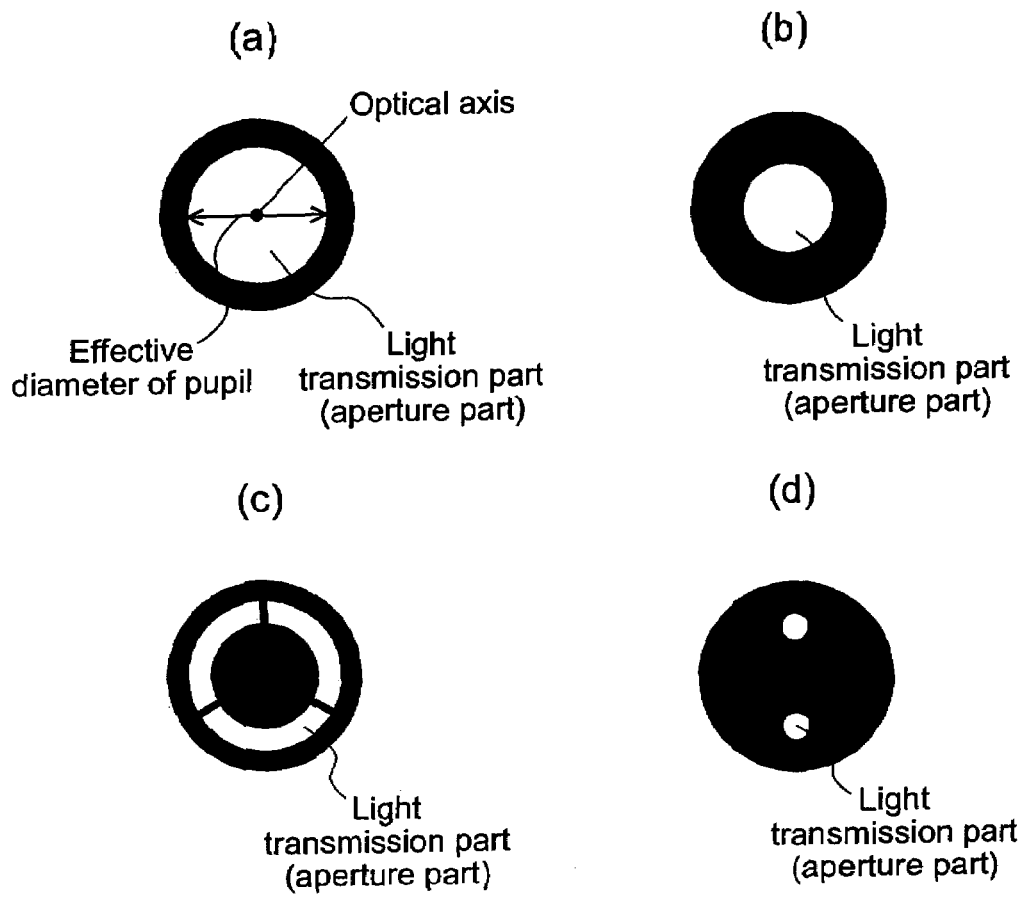
FIG. 5(a) is a diagram showing an example in which the aperture size of the aperture diaphragm is made as large as an effective diameter of a pupil part of the objective lens.
FIG. 5(b) is a diagram showing an example in which the size of the aperture of the aperture diaphragm is made smaller than the effective diameter of the pupil part of the objective lens.
FIG. 5(c) is a diagram showing an example of a filter that passes light in the peripheral part of the pupil part.
FIG. 5(d) is a diagram showing an example of a filter that passes a portion of light in the peripheral part of the pupil part.
Figure 6:
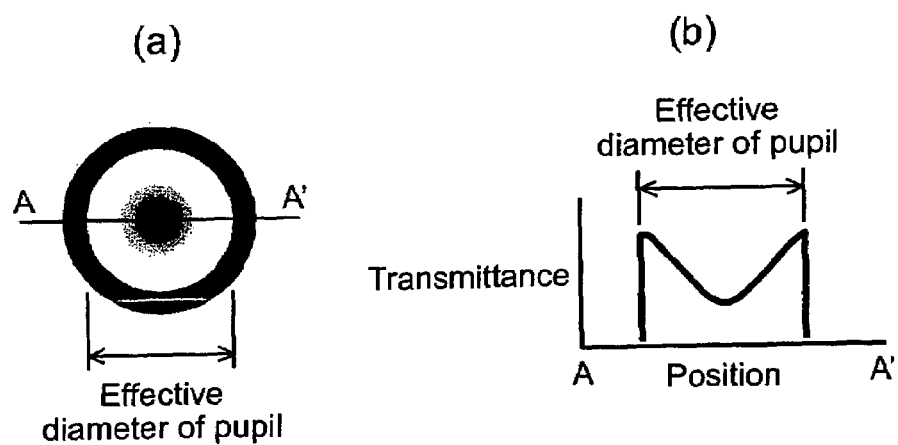
FIG. 6(a) is a diagram showing another example of an aperture diaphragm.
FIG. 6(b) is a graph showing the light transmittance in the A-A' section in FIG. 6(a).

FIG. 4 shows an example of the illumination means 3, which is composed of a laser light source 301, a shutter 302, a light quantity adjustment unit 303, a BS 304, a light quantity measurement unit 305, a beam enlargement unit 306, a beam formation unit 307, a coherence reduction unit 308, an aperture diaphragm 309, a pattern for A/F (A/F pattern) 310, and an unillustrated relay lens and mirror.

For the laser light source 301, any of the above mentioned light sources can be used. For example, the choice is a continuous oscillation laser of 266 nm (YAG-FHG).

The shutter 302 has a function of shielding the laser light emitted from the laser light source 301. For example, the shutter may be provided in the form of a metal plate that is driven by an unillustrated air cylinder, which is to be inserted in and extracted from the optical axis area.

The light quantity adjustment unit 303 may be any element capable of adjusting the quantity of light entering the BS 304, for example, an ND (Neutral Density) filter. The ND filter may be either of a target wavelength absorption type or a reflection type filter. However, since the absorption type filter is likely to be broken because of thermal expansion, it is preferable to use the reflection type. If the reflection type is used, it is advisable to add a laser trap in order to prevent the reflected light from entering the interior of the laser light source 301. Alternatively, a configuration that uses a wave plate and a PBS (polarizing beam splitter) by taking advantage of the polarization of the laser light source 301 may be adopted. This is a method of adjusting the quantity of light passing through the PBS by rotating the polarization direction using the half wave plate with respect to the incident light and, thereby, altering the polarization direction incident on the PBS.

Next, the BS 304 has a function of branching a portion of the incident light quantity into the light quantity measurement unit 305. The light quantity branched to the light quantity measurement unit 305 side may be roughly about 1-5% of the incident light quantity.

The light quantity measurement unit 305 has a function of measuring the light quantity branched from the BS 304, and, in response thereto, it controls the light quantity adjustment unit 303 or the laser light source 301 so that a value that conforms to an output value being set up is obtained in the input/output part 20.

The beam enlargement unit 306 has a function of expanding a beam emitted from the laser light source 301, for example, it operates as a beam expander.

The beam formation unit 307 has a function of adjusting the illumination range on the wafer 1. For example, if rectangular illumination is intended, a cylindrical lens is used.

The coherence reduction unit 308 has a function of reducing the coherence of the laser light, for example, it operates as a diffuser. In order to reduce coherence, since it is necessary to change the phase and angle of laser light both spatially and temporally, it is preferable to rotate the diffuser.

The aperture diaphragm 309 has a function of adjusting the illuminance distribution of the light that converges on the pupil part of the objective lens 8. FIGS. 5(a) to 5(d) show examples. FIGS. 5(a) to 5(d) show cross sections of the filters, along the optical axis, that are installed in the aperture diaphragm 309. FIGS. 5(a) to 5(d) are structures, each of which is provided with an aperture(s) in the light shielding plate, and the optical axis is in the central part of an outermost circle. FIG. 5(a) is an example in which the size of the aperture is set to be the same as the effective diameter of the pupil part of the objective lens 8. FIG. 5(b) is an example in which the aperture diameter in FIG. 5(a) is made smaller. Furthermore, FIG. 5(c) is an example of a filter that passes light in the peripheral part of the pupil part. FIG. 5(d) is an example of a filter that passes only a portion of light that is passes by the filter shown in FIG. 5C.

With these apertures, since the light is irradiated onto the wafer 1 from various angles, provided that an aperture of a wide range is used, there is an advantage of obtaining a stable image. Conversely, if the aperture is narrowed, there is an advantage of obtaining an image corresponding to a specific frequency on the wafer 1.

FIG. 6(a) shows another example of the aperture diaphragm 309. FIG. 6(a) shows an example in which the number of transmittance values is increased, whereas the examples shown in FIG. 5(a) to FIG. 5(d) are filters each having only two kinds of transmittance for an aperture(s) and a light shielding part. FIG. 6(a) shows an example in which the transmittance of light is continuously varied from the central part of the aperture to its peripheral part. FIG. 6(b) shows the transmittance in the A-A' cross-section in FIG. 6(a). In this example, the filter is specified to have lower refractive indexes in the central part of the aperture and higher refractive indexes in the peripheral part. In order to manufacture such a filter, for example, a dielectric film whose transmittance is varied may be deposited on a glass substrate. Alternatively, the transmittance may be varied by using a diffraction effect as a result of etching of a diffraction grating on a surface of the glass substrate. An advantage of the filter shown in FIG. 6(a) to FIG. 6(d) compared to the filter in FIG. 5(a) is that, since it can be designed so as to match an illuminance distribution of the illumination light, even when the illuminance distribution of the illumination light has a Gaussian distribution, the illuminance distribution can be flattened using a filter having a characteristic of the filter shown in FIG. 6(a) to FIG. 6(d). Conversely, an advantage of the filter in FIG. 5(a) is the capability of it being manufactured cheaply.

Figure 7:
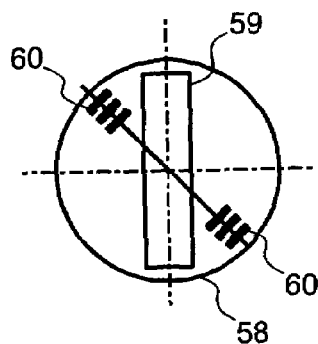
FIG. 7 is a diagram showing a pattern for A/F (auto focusing).

The A/F pattern 310 is a filter for projecting a pattern used for A/F on a sample surface. FIG. 7 shows a layout of the sample surface. In FIG. 7, the numeral 58 indicates a field of view of the objective lens 8, and the numeral 59 indicates an effective illumination range. On the other hand, the numeral 60 is an A/F pattern. This pattern 60 exists inside of the field of view 58, and it exists outside of the illumination range 59. The A/F pattern 310 may be manufactured by depositing a light shielding film in the form of the pattern 60 on a glass substrate.

In addition, it is preferable that a moving part of the components described above has a structure that does not transfer vibration, such as by use of a shock absorbing material etc.

The illumination means with a lamp light source will be explained with reference to FIG. 8.

Figure 8:
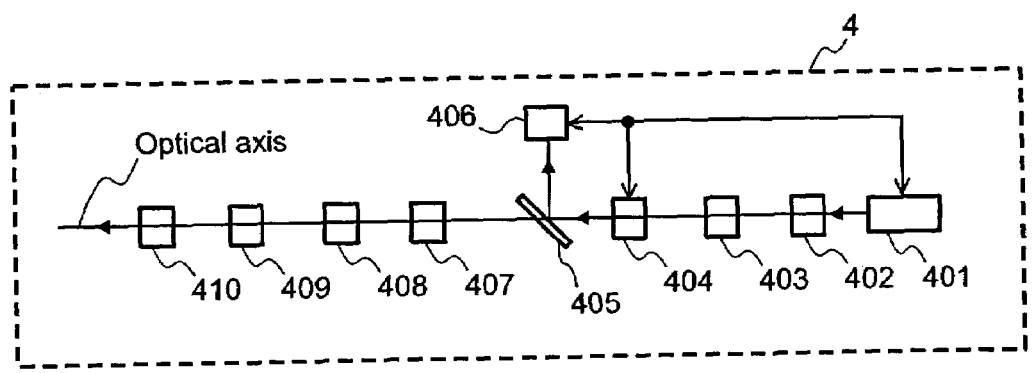
FIG. 8 is a diagram showing the structure of a lamp illumination means.

The illumination means shown in FIG. 8 is composed of a lamp light source 401, a shutter 402, a wavelength selection filter 403, a light quantity adjustment unit 404, a BS 405, a light quantity measurement unit 406, a beam enlargement unit 407, a beam formation unit 408, an aperture diaphragm 409, an A/F pattern 410, and an unillustrated relay lens and mirror.

For the lamp light source 401, one of the lamp light sources described above can be used.

The shutter 402, the light quantity adjustment unit 404, the BS 405, the light quantity measurement unit 406, the beam enlargement unit 407, the beam formation unit 408, the aperture diaphragm 409, and the A/F pattern 410 have the equivalent functions of counterparts of the illumination means using the laser light source that was explained in connection with FIG. 4. The counterparts in the illumination means using the laser light source are the shutter 302, the light quantity adjustment unit 303, the BS 304, the light quantity measurement unit 305, the beam enlargement unit 306, the beam formation unit 307, the aperture diaphragm 309, and the A/F pattern 310, respectively. The remaining parts will be described below.

The wavelength selection filter 403 is a filter that has a function of allowing a specific wavelength (having a band of ± a few nm) out of a plurality of wavelengths emitted from the lamp light source 401 to pass through it, and it is a commercially available product.

Next, the structure of the BS unit 6 will be explained. The BS unit 6 is made up of a PBS 601 (that reflects 90% or more of S polarization and passes 90% or more of P polarization), a non-polarizing BS 602 (that reflects or passes about 50% of both S polarization and P polarization), and partial PBS 603 (a BS such that a sum total of reflectance of S polarization and transmittance of P polarization exceeds 100%, for example, reflecting about 40% of S polarization and passing about 90% of P polarization), and one of them is selected by changeover (a changeover mechanism is not illustrated). Since these PBSs shall be used appropriately according to the surface state of the wafer 1, a component to be used may be determined at the time of setting up the inspection conditions.

Figure 9:
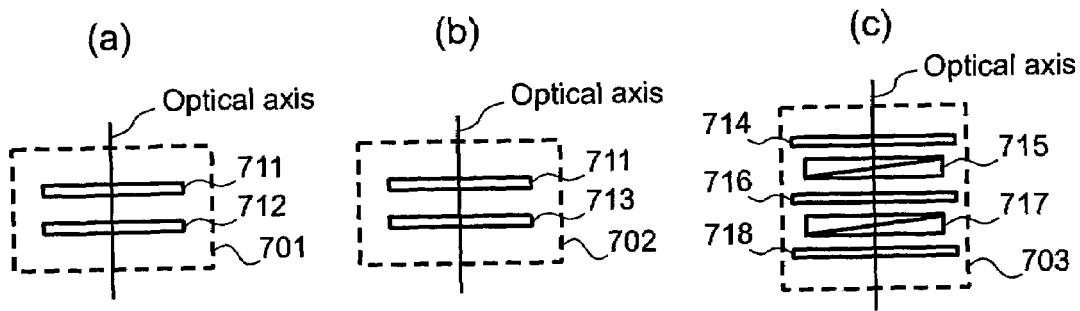
FIG. 9(a) is a diagram which shows an example in which the light modulation A unit is constructed with a half wave plate and a quarter wave plate.
FIG. 9(b) is a diagram which shows an example in which the light modulation A unit is constructed with a half wave plate and a special wave plate.
FIG. 9(c) is a diagram which shows an example in which the light modulation A unit is constructed with a half wave plate, a birefringent prism, and a quarter wave plate.

Next, the structure of the light modulation A unit 7 will be explained with reference to FIG. 9(a) to FIG. 9(c). In the light modulation A unit 7, one of units 701, 702, and 703 shown in FIGS. 9(a) to 9(c) is selected and used. FIGS. 9(a) to 9(c) will be explained below. FIG. 9(a) shows the unit 701, which consists of a half wave plate 711 and a quarter wave plate 712. Regarding its operation, first, the illumination light reflected by the BS unit 6 is incident on the half wave plate 711. The half wave plate 711 rotates the polarization direction of the illumination light. The illumination light thus rotated is converted into elliptically polarized light by passing through the quarter wave plate 712, and it is irradiated onto the wafer 1 via the objective lens 8. The illumination light is reflected and diffracted by the wafer 1, converged by the objective lens 8, and incident on the BS unit 6 via the quarter wave plate 712 and the half wave plate 711. At this time, the light reflected and diffracted by the wafer 1 suffers a different amount of change in its polarization state (the amount of rotation of polarization and a phase difference) between zero-order diffracted light and higher-order diffracted light. Therefore, the transmittance ratio of the zero-order diffracted light and the higher-order diffracted light in the BS unit 6 can be changed by rotating the half wave plate 711 and the quarter wave plate 712 around the optical axis with respect to the polarization direction of the diffracted light. Since the higher-order diffracted light contains edge information of a circuit pattern on the wafer 1, it becomes possible to enhance the contrast of the circuit pattern by detecting the higher-order diffracted light more than the zero-order diffracted light.

Figure 10:
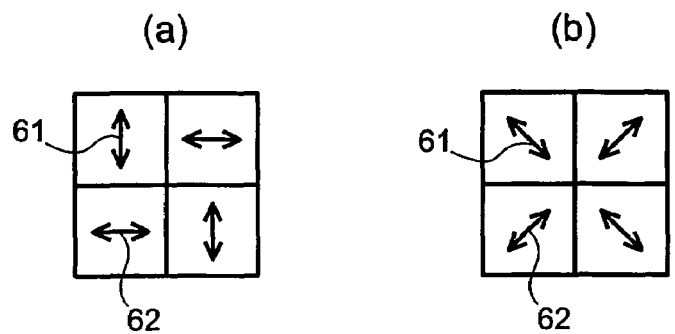
FIG. 10(a) and FIG. 10(b) are diagrams which show examples of special wavelength plates constructed by connecting quarter wave plates with different optic axes.

FIG. 9(b) shows the structure of the unit 702. The unit 702 is an example where a special wave plate 713 is used instead of the quarter wave plate 712. The structure of the special wave plate 713 will be explained with reference to FIGS. 10(a) and 10(b). FIG. 10(a) shows the composition of a quarter wave plate, having a certain optic axis 61, glued to a quarter wave plate having an optic axis 62 that is orthogonal to the optic axis 61. In order to manufacture this, for example, the quarter wave plates are glued to each other while arranged on fused quartz etc. FIG. 10(b) shows another embodiment of the special wave plate 713. In this example, the optic axis 61 crosses the optic axis 62 at right angles similar to the example in FIG. 10(a), but the directions of the optic axes relative to the optical axis are different from those in FIG. 10(a). By using the special wave plate 713, it becomes possible to allow the elliptical directions of the elliptical illumination to exist together, which enhances the contrast of rectangular patterns.

FIG. 9(c) shows the structure of the unit 703. The unit 703 in FIG. 9(c) consists of half wave plates 714, 716, birefringent prisms 715, 717, and a quarter wave plate 718. Each of the birefringent prisms 715, 717 is an optical component having a function of changing the propagation direction of the incident light according to the direction of the optic axis of the prism, which is for example, a Normaski-type prism. Next, its operation will be explained. The illumination light reflected by the PBS 6 is incident on the half wave plate 714. At this time, the polarization direction is rotated to a direction that makes a certain angle with the optic axis of the birefringent prism 715. The light, having passed through the birefringent prism 715, is divided to two axes parallel to the optic axis of the birefringent prism 715 and incident on the half wave plate 716. The half wave plate 716 rotates the polarization direction of the incident light to a direction that makes a certain angle with the optic axis of the birefringent prism 717 and makes it enter the birefringent prism 717.

Light, having passed through the birefringent prism 717, is divided in two axes parallel to the optic axis of the birefringent prism 717, so that a total of four light beams of liner polarization can be generated, including two divided directions by the birefringent prism 715. The four beams of linearly polarized light are incident on the quarter wave plate 718 and are irradiated onto the wafer 1 via the objective lens 8 as elliptically polarized light. A physical phenomenon by a polarization differential interference optical system using one Nomarski-type prism is equivalent to that of a common differential interference microscope.

A feature of the unit 703 of this invention is that it becomes possible to support rectangular patterns on the wafer 1 by dividing light into four or more light beams. That is, a normal prism capable of dividing light into two points has a differential interference effect only in a direction of a straight line connecting the two points. To improve this, a direction in which the light is branched into two beams by the birefringent prism 717 is set to be orthogonal to a direction in which the light is branched into two beams by the birefringent prism 715, whereby differential interference can be made to occur two-dimensionally. This scheme brings about an advantage in that differential interference can be realized regardless of the direction of the circuit pattern.

That is, the birefringent prisms 715, 717 are rotated around the optical axis, and the direction of polarization is rotated with the half wave plates 714, 716 so that the relationship described above is satisfied, whereby the branching direction of a light path can be changed. Thus, by changing the branching direction of the optical path in this way, defects of the circuit pattern in various directions can be inspected with a high sensitivity.

Incidentally, the light modulation A unit 7 has a structure that also allows for an optical element not to be inserted into the space between the BS unit 6 and the objective lens 8.

Figure 11:
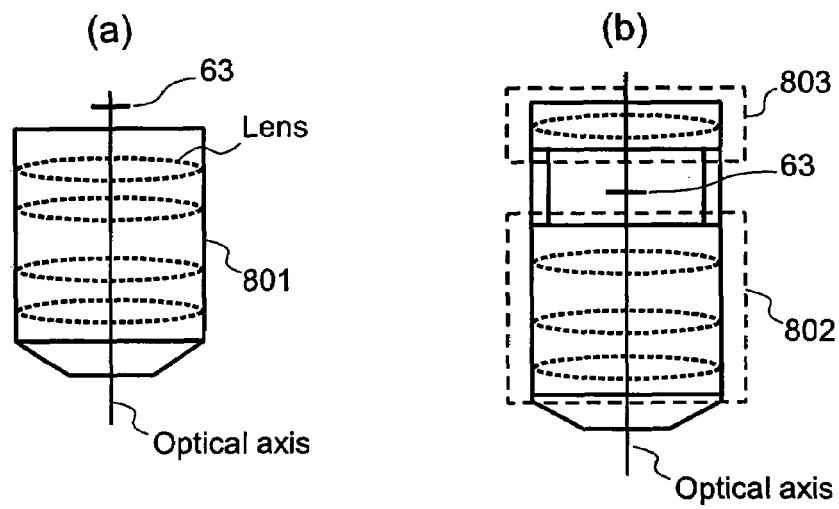
FIG. 11(a) is a diagram showing the structure of an objective lens whose pupil is outside its enclosure.
FIG. 11(b) is a diagram showing the structure of an objective lens whose pupil is inside its enclosure.

Next, the objective lens 8 will be explained. The objective lens 8 has a function of irradiating the illumination light which has passed through the light modulation A unit 7 onto the wafer 1 and of collecting reflected light and diffracted light from the wafer 1. A feature of the objective lens 8 in accordance with this invention is that it has a space in which the light modulation A unit 7 can be installed in a pupil point of the objective lens 8. That is, the objective lens 8 according to this invention has a configuration that enables the quarter wave plate and a special wave plate used in the light modulation A unit 7, as described above, to be installed in the pupil point. A specific example of the objective lens 8 that realizes this may involve a configuration in which a point of a pupil 63 of an objective lens 801 is set outside the enclosure of the objective lens 801, as shown in FIG. 11(*a*), or a configuration in which the objective lens 8 is divided into a sample surface side unit 802 and a BS unit 6 side unit 803, as shown in FIG. 11(*b*), and the pupil 63 is located between the sample surface side unit 802 and the BS unit 6 side unit 803.

The BS for A/F 9 has a function of branching the light which has passed through the BS unit 6 into the A/F detection unit 10 and the light modulation B unit 11. The AF detection unit 10 is a unit for measuring the amount of movement by which the Z position of the wafer 1 is moved to a focal point position of the objective lens 8.

The light modulation B unit 11 has a function of extracting certain light out of the transmitted light of the BS for A/F 9 or of passing the whole light. In FIG. 1, an optical element 1101 is an element for passing polarized light with a specific vibrating direction. The light modulation B unit 11 extracts specific light by inserting the optical element 1101 in the optical axis area. The optical element 1102 is made of glass, and it is inserted in the optical axis when no extraction of light by the optical element 1101 is performed.

The relay lens 12 has a function of forming a conjugate image of the pupil part of the objective lens 8 in a position of the light modulation C unit 13.

The light modulation C unit 13 has a function of modulating the phase and transmittance of light in the pupil conjugate position of the objective lens 8. Details of the light modulation C unit 13 will be explained with reference to FIGS. 12(*a*) to 12(*c*) and FIGS. 13(*a*) and 13(*b*). The light modulation C unit 13 is installed in a position conjugate to the pupil position of the objective lens 8, and it is used by selecting one from among the units 1301, 1302, and 1303.

Figure 12:
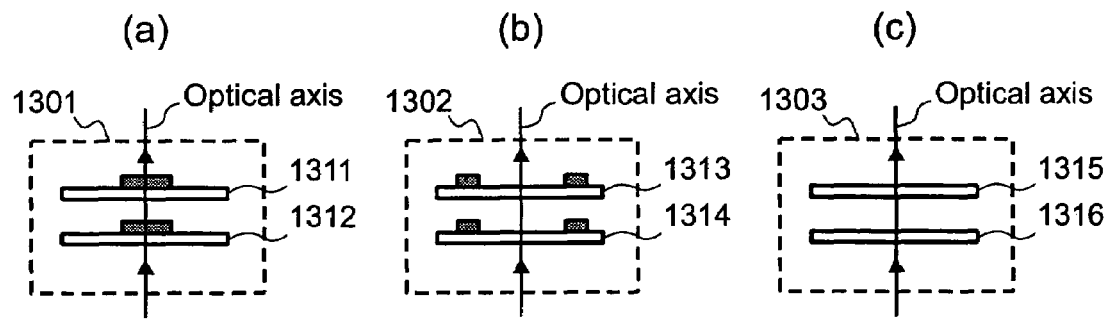
FIG. 12(a) is a diagram which shows an example in which the light modulation C unit is constructed with a spatial filter A and a spatial filter B.
FIG. 12(b) is a diagram showing an example in which the light modulation C unit is constructed with a spatial filter C and a spatial filter D.
FIG. 12(c) is a diagram which shows an example in which the light modulation C unit is constructed with two sheets of glass plates.
Figure 13:
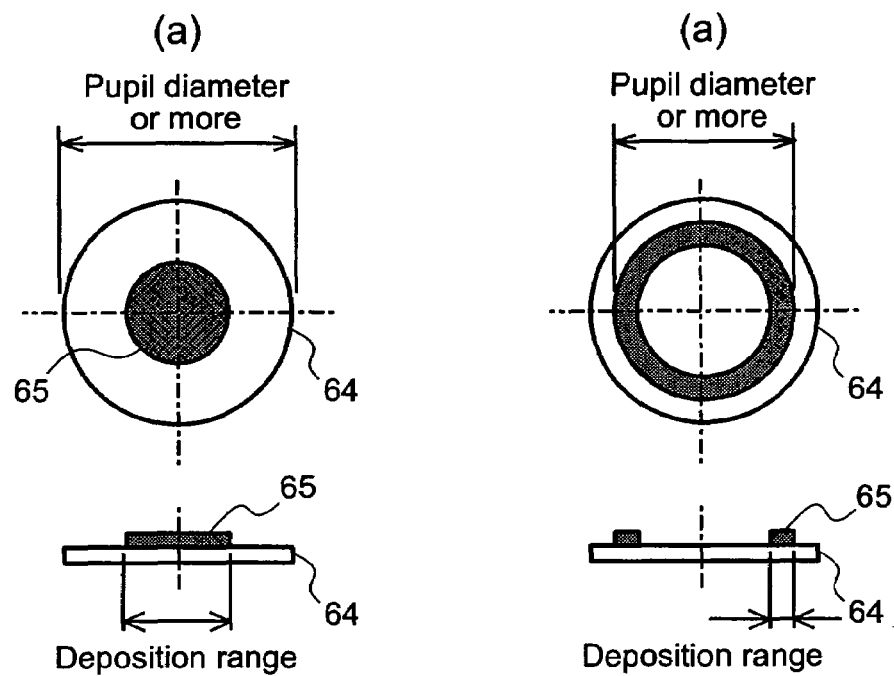
FIG. 13(a) is a top view and a cross section of the top view of the spatial filter A or B.
FIG. 13(b) is a top view and a cross section of the top view of the spatial filter C or D.

FIGS. 12(*a*) to 12(*c*) show an example of the light modulation C unit 13. FIG. 12(*a*) shows the unit 1301, which consists of a spatial filter A1311 and a spatial filter B1312. FIG. 13(*a*) shows the configuration of each of the spatial filter A1311 and the spatial filter B1312. The spatial filter A1311 has a transparent substrate 64, such as of quartz, on whose central part a dielectric film 65 is deposited. The dielectric film 65 is a film designed to produce a phase difference between transmitted light in a portion on which the dielectric film 65 is deposited and transmitted light in a portion on which no film is deposited. Moreover, the spatial filter B1312 has a transparent substrate on which a dielectric film is deposited, similar to the spatial filter A1311. The spatial filter B1312 is a film designed to produce a transmittance difference between transmitted light in a portion on which the dielectric film 65 is deposited and transmitted light in a portion on which no film is deposited. Here, the deposition range of the dielectric film 65 may correspond only to the size of the zero-order diffracted light in the pupil position. For this film, a film deposited such that its phase and transmittance are varied simultaneously may be used. In addition, the spatial filter A1311 and the spatial filter B1312 are not necessarily used simultaneously, and each of them may be used alone.

FIG. 12(*b*) shows the unit 1302, consisting of a spatial filter C1313 and a spatial filter D1314. FIG. 13(*b*) shows the configuration of each of the spatial filter C1313 and the spatial filter 1314. The spatial filter shown in FIG. 13(*b*) is used along with an annular filter as a pair at the aperture diaphragm 309 or aperture diaphragm 409. A feature of the spatial filter shown in FIG. 13(*b*) is that the deposition range of the dielectric film 65 of the spatial filter is in an annular form. The dielectric film 65 in FIG. 13(*a*) performs equally as well as the spatial filter A1311 and the spatial filter 1312, respectively.

FIG. 12(*c*) shows the unit 1303, which is composed of glass plates 1315, 1316. They are used when optical modulation with the unit 1301 or 1302 is not performed.

The light modulation C unit 13 has a mechanism (not illustrated) of selecting one from among the plurality of spatial filters shown in FIG. 12(*a*) or FIG. 12(*b*), that are prepared according to the shape of the illumination light.

An effect of the spatial filter of this invention is that the contrast of the circuit pattern can be enhanced, because it can decrease the intensity of the zero-order diffracted light of the wafer 1 and comparatively increase the intensity of higher-order diffracted light. An advantage of annular illumination is that it provides the capability of detecting much higher-order diffracted light, and, consequently, edge information of the circuit pattern can be enhanced compared to a case in which non-annular illumination is used.

The pupil observation unit 14 has a function of observing an image in a position of the light modulation C unit 13, and it is inserted in the optical axis using an unillustrated movable mechanism when observing the pupil image.

The imaging lens unit 15 has a function of forming an image of the wafer 1 in the light detection unit 17 under a plurality of magnifications, having a mechanism (not illustrated) of selecting one from among lenses 1501, 1502, and 1503 prepared in advance in the imaging lens unit 15 and inserting the selected lens in the optical axis area to change the magnification.

The sample surface observation unit 16 has a function of observing an image of a detected defect, and it is inserted in the optical axis using an unillustrated movable mechanism when observing defects.

The light detection unit 17 has functions of picking up an image of the wafer 1 by detecting light converged by the imaging lens unit 15 and A/D (analog-to-digital) converting it. The light detection unit 17 is, for example, an image sensor. More specifically, it may be provided on the form of a one-dimensional CCD sensor, a TDI (Time Delay Integration) image sensor, or photomultipliers arranged in series. Moreover, a two-dimensional CCD sensor, like a TV camera, may be used. An advantage of the TDI image sensor is that the SN ratio of detected signals can be improved by adding detected signals more than once. When using the TDI image sensor, it is preferable to drive the sensor in synchronization with the operation of the conveyance system 2.

As for optical components other than the ones used in the illumination means 3 and the illumination means 4, among the optical components described above, it is preferable for them to be aberration corrected at the wavelength emitted from the illumination means 3 and 4.

Figure 14:
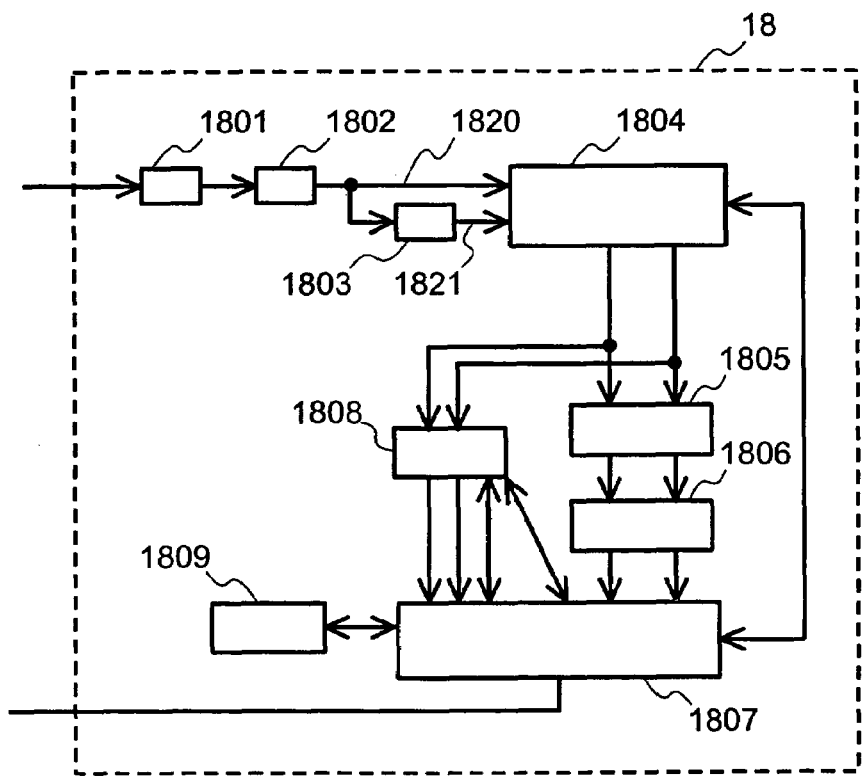
FIG. 14 is a block diagram showing the configuration of a signal processing circuit.

Details of the signal processing circuit 18 will be explained with reference to FIG. 14. The signal processing circuit 18 is composed of a gray scale conversion unit 1801, an image filter 1802, delay memory 1803, an alignment unit 1804, a local gray scale conversion unit 1805, a comparison processing unit 1806, a CPU 1807, a scatter diagram creation unit 1808, and storage means 1809.

More specifically, the detected signal obtained in the light detection unit 17 is sent to the signal processing circuit 18, and it is subjected to gray scale conversion, as described in JP-A No. 320294/1996, in the gray scale conversion unit 1801. This gray scale conversion unit 1801 compensates an image by logarithmic transformation, index transform, polynomial transform, etc. The image filter 1802 is a filter for efficiently removing image noise peculiar to the illumination light source from an image signal whose gray scales were converted in the gray scale conversion unit 1801. The delay memory 1803 is a memory unit for storing reference image signals, and it delays output signals from the image filter 1802 by storing the output signals corresponding to one cell, or a plurality of cells, or a die, or a plurality of dies, that repeats itself (themselves) to constitute a semiconductor wafer. Here, a cell is a repeating unit of the pattern within the die. Note that the image filter 1802 may be placed downstream the delay line 1803.

Next, the position alignment unit 1804 detects the amount of offset between an image signal 1820 (detected image signal obtained from the wafer 1) outputted from the gray scale conversion unit 1801 and a delayed image signal 1821 (reference image signal serving as a reference) obtained from the delay memory 1803 by a normalized correlation method etc., and it performs pixel-to-pixel alignment. The local gray scale conversion unit 1805 is used for converting gray scales on both or either of the image signals that are different in feature quantities (brightness, derivative value, standard variation, texture, etc.), so that the feature quantities become consistent.

The comparison processing unit 1806 compares the detected image signals whose gray scales were converted by the local gray scale conversion unit 1805 and detects defects based on differences in the feature quantities. That is, the comparison processing unit 1806 compares the reference image signal, that is outputted from the delay memory 1803 and delayed by an amount corresponding to a cell pitch, and the detected image signal. By having inputted coordinates of array data etc. on the wafer 1 from the input/output part 20, the CPU 1807 creates defect inspection data based on coordinates of the array data on the wafer 1 etc., and it stores this data in the storage means 1809. The defect inspection data is sent to the input/output part 20 and the ADC unit 19, as required. The comparison processing unit 1806 may be as disclosed in JP-A No. 212708/S61. For example, it is composed of an image position alignment circuit, an image-difference detection circuit of aligned images, a circuit for binarizing a difference image and detecting disagreement, and a feature extraction circuit for calculating area, length (projected length), coordinates, etc. from a binarized output.

The scatter diagram creation unit 1808 has a function of creating a scatter diagram of the feature quantity of the detected image from the input image and the feature quantity of the reference image, and it displays this diagram in the input/output part 20 via the CPU 1807.

FIG. 15 shows an example of a sequence of operation of the signal processing circuit 18. First, the SN ratios of the detected and reference images that were inputted are improved by noise reduction processing in Step S1901, as required. Various filtering methods are available for noise reduction and can be chosen according to a target object and the property of the noise. For example, there are a method of using values of neighboring pixels with weights instead of an individual pixel, i.e., the median filtering, and a method of removing noise occurring periodically by using Fourier transform.

Next, the reconstruction processing Step S1902 of an image whose quality has been degraded by noise reduction is performed. For example, it involves reconstruction processing using a Wiener filter.

Next, it is determined whether there is a large difference in the image quality between the detected image and the reference image that are to be compared. Evaluation indexes include contrast, dispersion (standard deviation) of brightness, frequencies of noise components, etc. The evaluation indexes of an image are calculated in processing Step S1903 for calculating the feature quantities, and image merging processing Step S1905 is performed based on the results of the processing Step S1904 for comparing calculated feature quantities. If the image is not at a level which enables alignment of the two images with the feature quantities, the detection sensitivity is decreased in the comparison processing unit 1807 so that the occurrence of false information is prevented. Subsequently, the defect detection and determination Step S1906 is performed. Incidentally, regarding a detailed method of calculating defects in the signal processing circuit 18, for example, a method as disclosed in JP-A No.194323/2001 may be employed.

Next, the input/output part 20 will be explained. The input/output part 20 is an interface unit that allows an interface with the user, and it also functions to provide input/output of data and control signals. Here, inputs from the user, for example, may include layout information and a name of an inspection target wafer, and inspection conditions of the optical system described above, etc. Output information to the user, for example, may include results of defect inspection, images of detected defects, etc.

The ADC unit 19 has a function of classifying signals detected by the inspection apparatus of this invention. Operations of the ADC unit 19 will be explained. First, an image obtained in the light detection unit 17 is transmitted to the signal processing circuit 18 and the ADC unit 19. The signal processing circuit 18 performs defect detection and determination on the image. If the image is determined to be defective, a defect detection flag and an image that was processed in the signal processing circuit 18 are transmitted to the ADC unit 19. When receiving the defect detection flag, the ADC unit 19 calculates image feature quantities of a defective part from an image obtained in the light detection unit 17 and the image transmitted from the signal processing circuit 18, and it further calculates and classifies coordinate feature quantities from coordinate data of the conveyance system 2 transmitted from the controller 21. The classified information is transmitted to the input/output part 20 and displayed as defect information.

Here, the image feature quantities are a total sum of gray scale values in the defective part, a spatial variation of the gray scale value (derivative value), the number of pixels, a projected length, the position of the center of gravity, gray scale values in a normal part that was compared, etc. Moreover, the coordinate feature quantities include a distance from the center of the wafer 1, the number of repetition of dies in the wafer 1, a position within the die, etc.

Furthermore, since the use of the optical system of this invention enables acquisition of an image under various optical conditions, feature quantities calculated from an image detected under optical conditions different from those at the time of defect detection can be used for classification. For example, under conditions (condition A) where a PBS is installed in the BS unit 6, the light modulation A unit 7 is set for circularly polarized illumination, and optical components are installed in neither the light modulation B unit 11 nor the light modulation C unit; whereby, an image equivalent to that in a normal bright field microscope can be acquired. Under conditions (condition B) where a unit of the birefringent prism is inserted in the light modulation A unit 7, information of pattern height is obtained. Therefore, by classifying two-dimensional sizes by the condition A and classifying the height by the condition B, a three-dimensional form of a foreign material etc. can be classified.

Although the above-mentioned embodiment involves a case where a laser is used as illumination means 3 and a lamp light source is used as the illumination means 4, the illumination means 3 and 4 both may be laser light sources oscillating laser lights whose wavelengths are mutually different, or they both may be lamp light sources emitting lights whose wavelengths are mutually different. Furthermore, the above-mentioned embodiment involves a case where the illumination means 3 and the illumination means 4 have different wavelengths. Alternatively, the following scheme may be adopted: only one illumination means that consists of a lamp light source or a laser light source emitting white light in a broad wavelength band or having a plurality of bright lines is used, the light emitted from this illumination means is divided into a plurality of lights using wavelength dividing means, the light quantities of the divided lights are detected, and respective light quantities are adjusted using light quantity adjusting means that corresponds to the light quantity adjustment unit 303 or 404.

Figure 18:
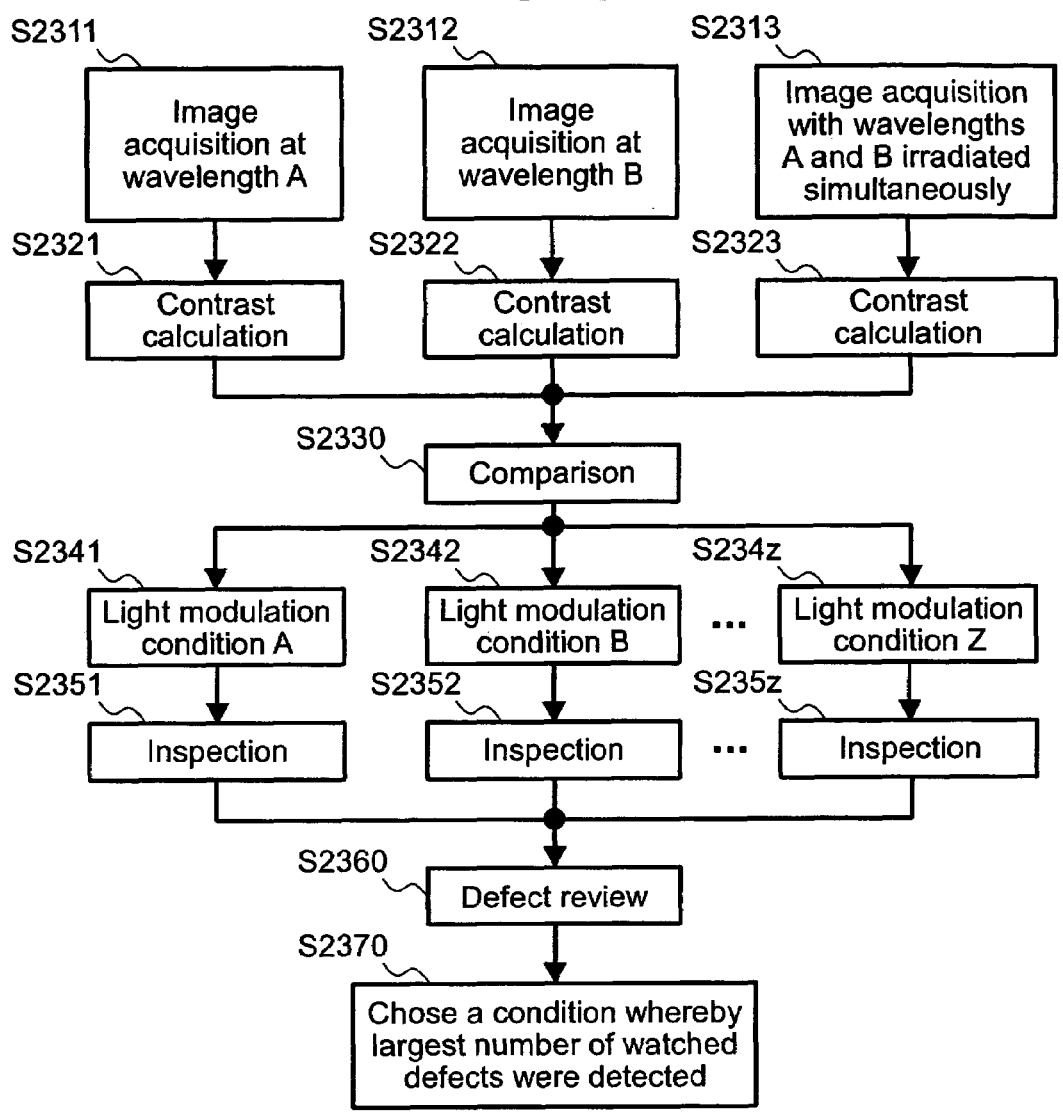
FIG. 18 is a process sequence diagram showing a procedure of setting up inspection conditions.

Next, a method of setting up the inspection conditions in accordance with this invention using the above-mentioned inspection apparatus will be explained with reference to FIGS. 16 to 18. FIG. 16 shows an example of a condition setting screen used in the inspection apparatus of this invention. The setting screen which forms the example shown in FIG. 16 is made up of a device name registration part 2101, a process name registration part 2102, a watched area data registration part 2103, a process rule registration part 2104, and an inspection-layer information registration part 2105. Details concerning the setting screen will be explained below.

The device name registration part 2101 and the process name registration part 2102 are provide for registering keywords used when calling up the contents registered on the screen of FIG. 16 at a later time, and any name may be used as long as it provides recognition of the contents later. The watched area data 2103 specifies an area to be inspected in the wafer 1. The watched area data 2103 does not necessarily need to be set up. The setting is required, for example, when an inspection area is to be decreased in order to shorten the inspection time, or when the inspection sensitivity is to be altered for each circuit pattern formed in the wafer 1, or when a characteristic of a defect to be detected is to be changed for each location in the wafer 1.

The process rule registration part 2104 is used for describing a rule of manufacture of the circuit pattern of the inspection target wafer. For example, it may specify that the is 180 nm, 90 nm, etc.

The inspection layer information registration part 2105 is a part in which a state of the uppermost surface of the inspection target wafer is chosen. This invention facilitates the ability of the user to choose a state of the wafer from states that are often chosen for inspection. The information chosen in the inspection layer information registration part 2105 determines the optical conditions in a correspondence table that is saved in advance inside the inspection apparatus of this invention. FIG. 17 shows an example of the correspondence table. Although it is preferable to register the correspondence table in advance in the inspection apparatus of this invention, the user may create it using the apparatus of this invention, or download it from an external storage connected to the inspection apparatus of this invention.

The correspondence table of FIG. 17 shows different types of inspection layer information in vertical columns and optical conditions that can be altered in various parts of the inspection apparatus of this invention along it's the horizontal lines during sequential steps in the manufacture. For example, since the illumination wavelength can be chosen from two kinds of wavelengths, the user is allowed to chose a wavelength of the illumination means 3, a wavelength of the illumination means 4, or simultaneous illumination by the illumination means 3 and the illumination means 4. The column of aperture diaphragm values includes choices in the aperture diaphragm 309 or 409. The column of light modulation conditions sets forth choices of the light modulation A unit 7, the light modulation B unit 11, and the light modulation C unit 13. Moreover, similarly, a correspondence table that describes choices in the BS unit 6 and choices in the imaging lens unit 15 has also been created. Which technology is chosen for which inspection layer information may be allocated by analyzing a physical phenomenon, or it may be determined using optical simulation, or by actually inspecting the wafer.

A method of setting up conditions by actually inspecting a wafer will be explained with reference to FIG. 18. To conduct condition setting, first, an illumination wavelength is determined. A method which can be used for this determination is as follows: first, only the wavelength A of the illumination means 3 is used to acquire an image of the circuit pattern (Step S2311), and the contrast is calculated (Step S2321). Next, only the wavelength B of the illumination means 4 is used to acquire an image of the circuit pattern (Step S2312), and the contrast is calculated (Step S2322). Finally, the wavelengths A and B of the illumination means 3 and 4 are irradiated simultaneously to acquire an image of the circuit pattern (Step S2313), and the contrast is calculated (Step S2323). The contrasts determined for these three kinds of conditions are compared (Step S2330), and an illumination condition that gives the highest contrast is determined as the illumination condition for the wafer.

Next, an optical modulation condition that is settable by the inspection apparatus of this invention is set up and the inspection is performed. First, it is set to the optical modulation condition A (Step S2341) to perform inspection (Step S2351). Next, it is set to the optical modulation condition B (Step S2342) to perform inspection (Step S2352). This operation is performed until a light modulation condition Z is carried out. In this inspection, the whole wafer surface may be inspected. However, for purposes of shortening the time to set up the inspection condition, inspection may be limited to several dies therein. What is necessary next is to review the inspection results under the above-mentioned light modulation conditions (Step S2360) and choose a condition that has detected a maximum number of watched defects (Step S2370). At this time, review of inspection may be performed at each time of inspection completion, but a review based on a result of the sum of all inspection results makes it possible to carry out a review in a short time. With the procedure mentioned above, condition setting is ended.

Although a procedure to set up conditions was described above, a different optical condition may be set up for each inspection location in the wafer as an item other than the specific steps described above. In this case, after performing a plurality of inspections, a sum of the individual inspection results is outputted.

Moreover, if the intensity of the illumination wavelength emitted from the illumination means 3 or 4 that causes damage on the wafer 1 is known, an illumination intensity causing no damage is calculated and the wafer 1 is illuminated using that intensity. Whether it causes damage may be inferred from the inspection layer information. It is advisable that, if the illumination light quantity is low and the signal quantity from a defect is insufficient, the gain of the optical detector 17 is increased to obtain a signal quantity necessary for inspection.

Figure 19:
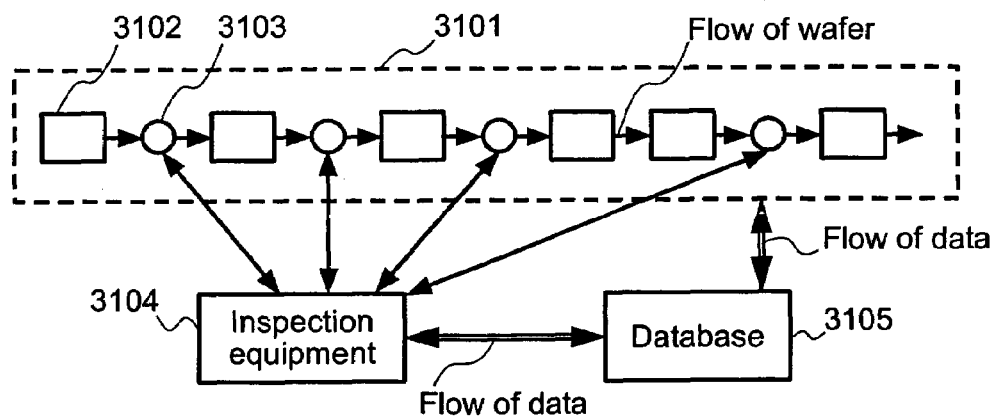
FIG. 19 is a diagram showing an example in which the inspection apparatus of this invention is applied to a semiconductor device production line.

Next, a method of using the inspection apparatus of this invention will be explained. FIG. 19 is a diagram showing a semiconductor device production line and an inspection apparatus of this invention. FIG. 19 shows part of a whole process 3101 at the time of device manufacture, which is made up of a device manufacture process 3102, an inspection process 3103, an inspection apparatus 3104 of this invention, and a database 3105. In the device manufacture, the wafer is processed according to the manufacturing process 3101. In manufacturing the device, an inspection process is added in order to check the quality of the processing. The wafer inspected in this inspection process 3103 has various surface states depending on its manufacturing process. For example, the wafer might be in a state after resist coating, a state after deposition of the insulator film, a state after etching of the insulator film, a state after deposition of a metal film, and a state after etching of the metal film. In these various surface states, the inspection apparatus must be capable of inspecting the wafer with a high sensitivity.

The conventional inspection apparatus deteriorates in performance depending on the manufacturing process 3102 because the settable optical conditions are limited. With the inspection apparatus 3104 of this invention, the optical conditions can be optimized according to the process state; therefore, high-sensitivity inspection in each inspection process becomes possible with only one inspection apparatus, and occurrence of a defect in a semiconductor device production line can be monitored properly. Here, as described above, the user may register information necessary to set up inspection conditions. However, the following scheme may be adopted: the inspection apparatus acquires process information from the database 3105 which is accessible connectable to information of the whole process 3101 at the time of device manufacture, which is used to set up the inspection conditions.

Second Embodiment

Figure 20:
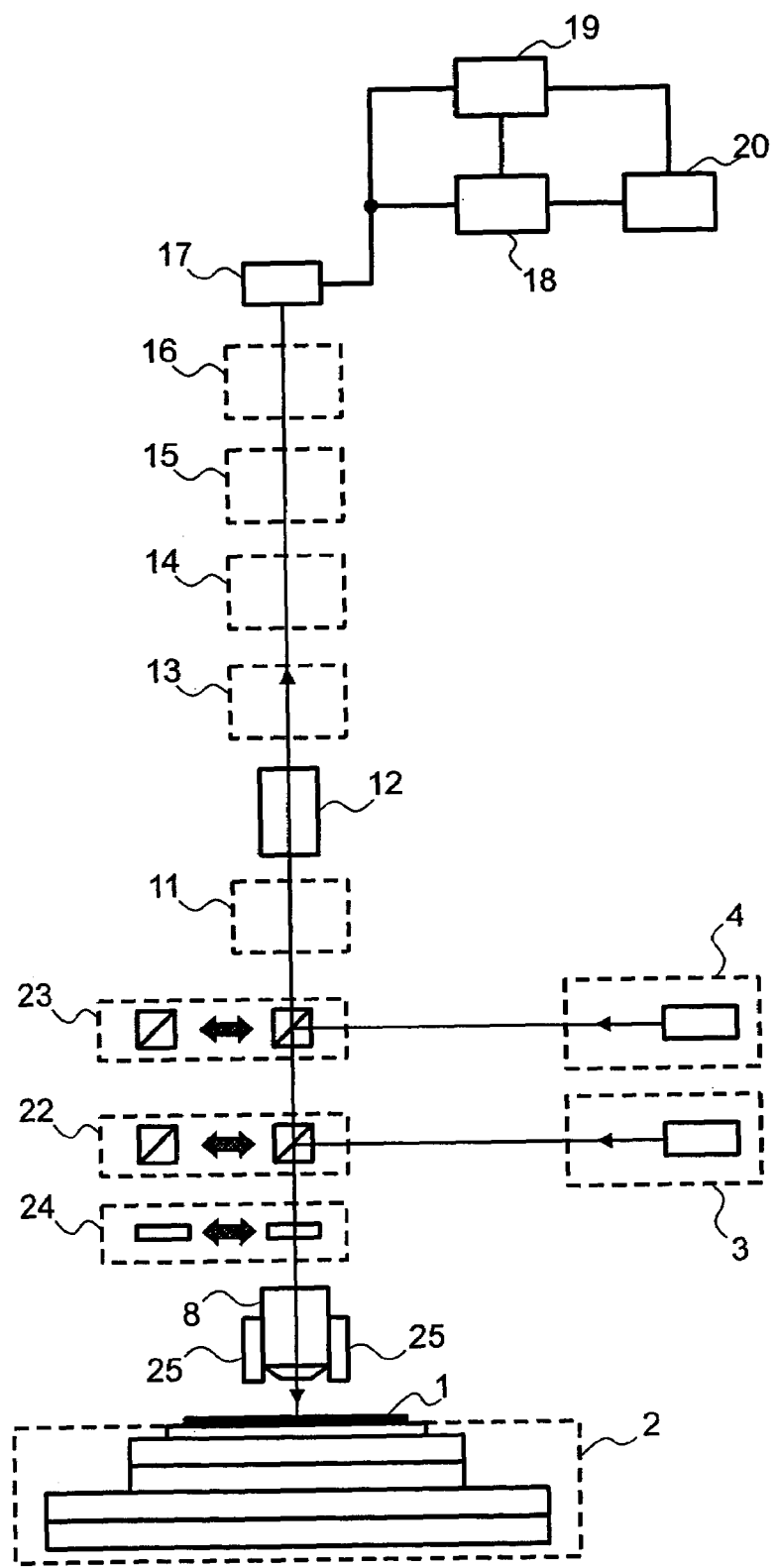
FIG. 20 is a diagram showing an outline of the structure of a second embodiment of the pattern defect inspection apparatus in accordance with the present invention.

Another embodiment of the pattern defect inspection apparatus according to this invention is shown in FIG. 20. The pattern defect inspection apparatus of this invention is composed of: a conveyance system 2 that supports the inspection target wafer 1 and moves it, the illumination means 3 and 4 whose wavelengths are different, the BS units 22 and 23, the light modulation A unit 24, the objective lens 8, the A/F unit 25, the light modulation B unit 11, the relay lens 12, the light modulation C unit 13, the pupil observation unit 14, the imaging lens unit 15, the sample surface observation unit 16, the light detection unit 17, the signal processing circuit 18, the ADC unit 19, the input/output part 20, and an unillustrated controller, relay lens, and mirror.

This embodiment is different from the configuration explained in connection with Embodiment 1 in terms of the performance of the optical elements used in the BS units 22 and 23, the performance of the optical elements used in the light modulation A unit, and the method of operation of the A/F unit 25.

First, the BS units 22 and 23 will be explained. A PBS used in the BS unit 6 shown in Embodiment 1 has a characteristic as shown in FIG. 21(a). FIGS. 21(a), 21(b), and 21(c) are graphs each showing the transmittance of the PBS as a function of wavelength. Wavelengths A and B represent wavelengths used in Embodiment 1, and FIG. 21(a) shows a case where, with one PBS, a similar performance (transmittance of P polarization and S polarization) is obtained at the wavelengths A and B.

On the other hand, Embodiment 2 represents an example in which a PBS having the performance shown in FIG. 21(b) and FIG. 21(c) is used. FIG. 21(b) shows that the PBS has a performance such that the transmittance of P polarization is high and the transmittance of S polarization is low (high reflectance) at the wavelength A, and the transmittance of P polarization is high and the transmittance of S polarization is also high at the wavelength B. Moreover, FIG. 21(c) shows that the PBS has a performance such that the transmittance of P polarization is high and the transmittance of S polarization is also high at the wavelength A, and the transmittance of P polarization is high and the transmittance of S polarization is low at the wavelength B. Generally, it is difficult to design the transmittance and reflectance to desired values in a wide range of the wavelength band. Therefore, if the PBSs having the characteristics shown in FIGS. 21(b) and 21(c) are used, a cheaper apparatus can be produced than is possible using the PBS having the characteristics shown in FIG. 21(a).

An example of a configuration using the BS having the performance shown in FIGS. 21(b) and 21(c) is the following case. Assuming that the wavelength A and the wavelength B in FIGS. 21(a) and 21(b) are emitted from the illumination means 3 and from the illumination means 4, respectively, if a BS with a performance equivalent to the performance shown in FIG. 21(b) is used in the BS unit 22 and a BS with performance that conforms to the performance shown in FIG. 21(c) is used in the BS unit 23, the BS unit 22 and the BS unit 23 can satisfy the performance requirements of the PBS at both wavelengths, respectively.

Next, the light modulation A unit 24 will be explained. FIG. 22 shows one example of the light modulation A unit 24. The light modulation A unit 24 in FIG. 22 consists of the half wave plates 2401, 2403 and quarter wave plates 2402, 2404.

FIGS. 23(a) and 22(b) show the performance of the wave plates used in the unit 24 of FIG. 22. FIG. 23(a) shows the performance of the half wave plate 2401, and FIG. 23(*b*) shows the performance of the half wave plate 2403. FIGS. 23(*a*) and 23(*b*) show the performance of a phase difference between optic axes of the half wave plates as a function of wavelength, respectively. That is, FIG. 23(*a*) shows that the light modulation A unit 24 satisfies the performance of a half wave plate for light of the wavelength A, but exhibits a performance equal to that of a glass plate at the wavelength B. On the other hand, FIG. 23(*b*) shows that the light modulation A unit 24 exhibits a performance equal to that of a glass plate, but satisfies the performance of a half wave plate at the wavelength B. In Embodiment 1, for the half wave plate 701, the wave plate that satisfies the performance of a half wave plate at both wavelengths A and B (wavelengths emitted from the illumination light sources 3 and 4) is used. On the contrary, in this embodiment, wave plates that satisfy the performance of a half wave plate at either of the wavelengths, respectively, are used. In the case where it is difficult to satisfy the performance of a half wave plate in wavelengths of a wide band, as in the case of the BS described above, the wave plates as provided in this embodiment are used. In this explanation, a half wave plate is described, but the situation is also the same when using a quarter wave plate.

Next, the A/F unit 25 will be explained. The A/F unit 25 is a mechanism that projects a pattern on the wafer 1 from outside of the NA of the objective lens 8, picks up reflected light of the projected pattern using a CCD line sensor, etc., and adjusts the surface of the wafer 1 to a focal point position of the objective lens 8. A pattern form to be projected and its position may be as described with reference to FIG. 7. It is preferable for the wavelength of the light source used in the A/F unit 25 to be different from the wavelengths emitted from the illumination means 3 and 4.

Third Embodiment

Figure 24:
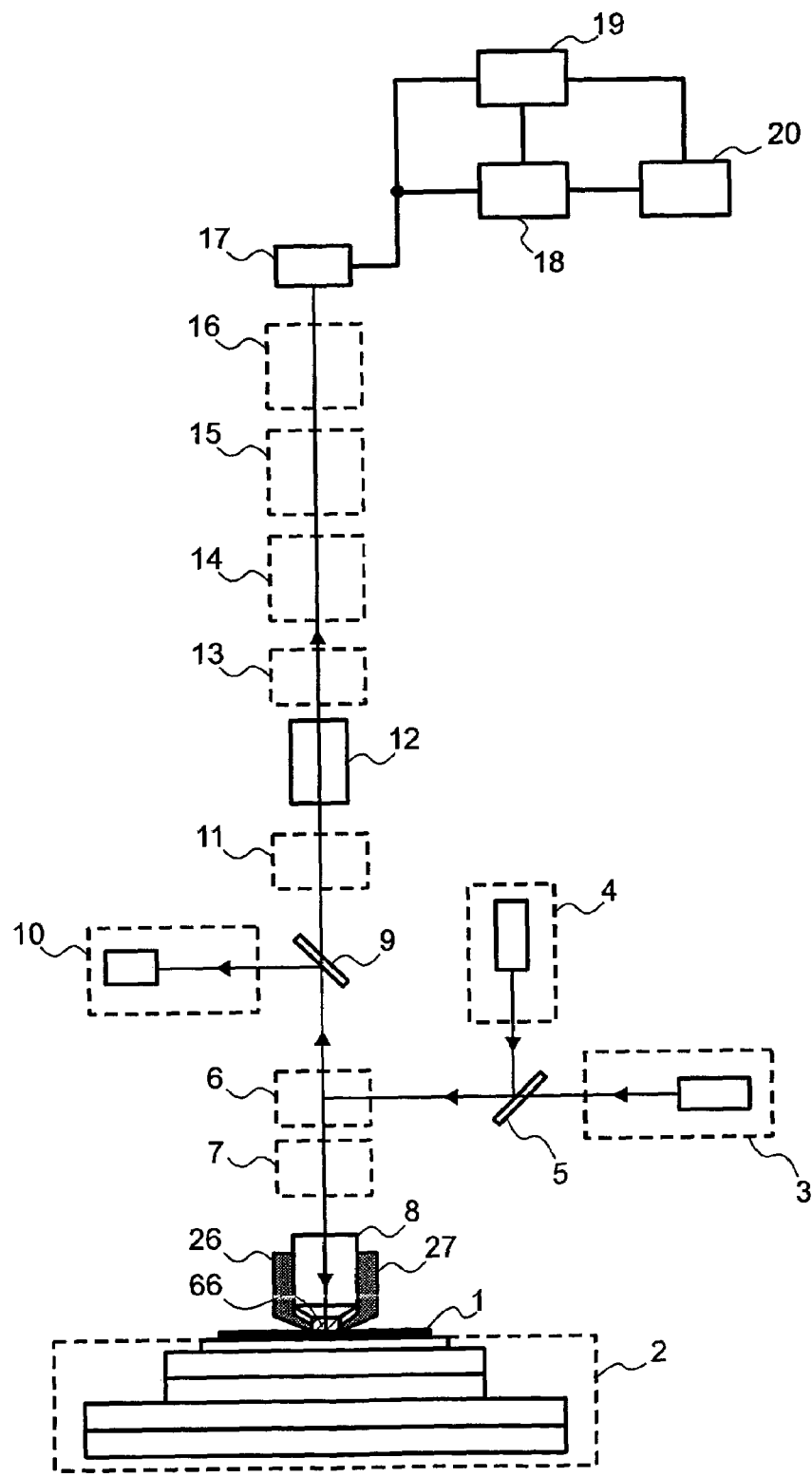
FIG. 24 is a diagram showing an outline of the structure of a third embodiment of the pattern defect inspection apparatus in accordance with the present invention.

Another embodiment of the pattern defect inspection apparatus according to this invention is shown in FIG. 24. The basic configuration of the pattern defect inspection apparatus of this embodiment is the same as that of Embodiment 1. This embodiment is constructed with a water injection system 26 and a drainage system 27, in addition to the configuration of Embodiment 1.

Next, details of the water injection system 26 and the drainage system 27 will be explained. The water injection system 26 has a function of supplying a medium 66 to a gap between the wafer 1 and the objective lens 8, and the drainage system 27 has a function of removing the medium 66 supplied to the gap between the wafer 1 and the objective lens 8. Here, the medium 66 has a refractive index that is larger than that of air (1<refractive index, preferably the refractive index is close to the refractive index of $SiO_2$ etc. at the illumination wavelength) and causes no damage to the wafer 1. For example, this may be pure water as regularly used in semiconductor factories.

The object of this embodiment is to provide a high-sensitivity pattern defect inspection apparatus that is realized both by optical noise reduction using a technique of reducing thin film interference caused by a transparent thin film, such as an insulator film, that is deposited on an LSI and by resolution improvement resulting from a higher NA of the objective lens.

A principle whereby the above-mentioned effect is obtained will be explained. Basically, thin film interference occurs in any interface where the refractive index changes. For example, when light is incident on an insulator film using a refractive index of 1.5, thin film interference takes place at an interface with air whose refractive index is 1. A feature of this embodiment lies in the fact that air between the objective lens and the wafer is removed, and the gap is filled with a medium whose refractive index is about 1.5 instead, whereby a part at which the refractive index changes is eliminated and thin film interference is reduced. Moreover, the NA of the objective lens is proportional to the refractive index of the medium disposed between the objective lens and the wafer. Therefore, an increase in the refractive index of the medium between the objective lens and the wafer, as described above, can improve the NA, which will provide a detected image with high resolution.

In the embodiment shown in FIG. 24, an example in which the medium 66, such as pure water, is supplied locally between an undersurface of the objective lens 8 and the wafer 1 has been considered. The whole wafer may be immersed in the medium 66 using unillustrated means, so that the system is configured to further immerse the undersurface of the objective lens 8 in the medium 66.

If the apparatus is configured as described above, it is possible to inspect various LSI patterns for defects at a high speed and with a high sensitivity. Incidentally, the features described in connection with each embodiment can be used also in other embodiments. In the embodiments described above, a case where two kinds of wavelengths are used has been considered, but it is not necessary to use two kinds of wavelengths. The light modulation unit can be applied even when only one kind of wavelength is used. The invention is also applicable to the use of three or more kinds of wavelengths. In this case, optical elements with corrected wavelength characteristics (aberration, reflectance characteristic, etc.) are used.

Moreover, each light modulation unit may be used alone or in a combined manner.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for inspecting defects of a pattern, comprising:
   illumination means for illuminating a sample on whose surface a pattern was formed;
   imaging optical system means for forming an optical image of the pattern of the sample illuminated by the illumination means;
   detecting means for detecting an optical image of the pattern of the sample by detecting the optical image formed by the imaging optical system means;
   defect detecting means for detecting pattern defects on the sample by processing the detected image by the detecting means; and
   selecting means for selecting a combination of an illumination wavelength of the illumination means and an aperture diaphragm of the illumination means and/or the imaging optical system according to the pattern,
   wherein, prior to detecting pattern defects, said defect detecting means processes the images detected by the detecting means to reduce noise, and reconstructs noise reduced images that have been degraded by the noise reduction process.

2. The apparatus for inspecting pattern defects according to claim 1, wherein
the illumination means is equipped with a plurality of illumination light sources,
the plurality of illumination light sources including a lamp light source and a laser light source.

3. The apparatus for inspecting pattern defects according to claim 1, wherein
the illumination means is equipped with a lamp light source.

4. The apparatus for inspecting pattern defects according to claim 1, wherein
the illumination means includes a laser light source.

5. The apparatus for inspecting pattern defects according to claim 1, wherein
the illumination means has a plurality of illumination light sources having different wavelengths,
an intensity measurement unit for measuring respective intensities of the plurality of illumination light sources,
an intensity measurement unit that adjusts intensities of lights emitted from the plurality of illumination light sources so that a ratio of intensities of the plurality of illumination light sources measured by the intensity measurement unit becomes constant.

6. An apparatus for inspecting pattern defects, comprising:
illumination means for illuminating a sample on whose surface a pattern was formed;
imaging optical system means for forming an image of diffracted light from the sample illuminated by the illumination means;
light modulating means that is disposed in an optical path of the illumination means and/or the imaging optical system means and controls the intensity and/or phase of the light;
image detecting means for picking up an image of diffracted light from the sample that is formed by the imaging optical system means and outputting the image signal; and
defect detecting means for detecting defects of a pattern formed on the sample by processing the image signal outputted from the image detecting means,
wherein, prior to detecting pattern defects, said defect detecting means processes the images detected by the image detecting means to reduce noise, reconstructs the noise reduced images that have been degraded by the noise reduction process.

7. The apparatus for inspecting pattern defects according to claim 6, wherein
the illumination means is equipped with a plurality of illumination light sources,
the plurality of light sources containing a lamp light source and a laser light source.

8. The apparatus for inspecting pattern defects according to claim 6, wherein
the illumination means is equipped with a lamp light source.

9. The apparatus for inspecting pattern defects according to claim 6, wherein
the illumination means contains a laser light source.

10. The apparatus for inspecting pattern defects according to claim 6, wherein
the illumination means has a plurality of illumination light sources whose wavelengths are different,
an intensity measurement unit for measuring intensities of the plurality of illumination light sources,
and an intensity adjustment unit that adjusts the intensities of lights emitted from the plurality of illumination light sources so that a ratio of the intensities of the plurality of illumination light sources measured by the intensity measurement unit becomes constant.

11. The apparatus for inspecting pattern defects according to claim 6, wherein
the light modulating means is equipped with a half wave plate and a quarter wave plate.

12. The apparatus for inspecting pattern defects according to claim 6, wherein
the light modulating means is equipped with a differential interference optical system.

13. The apparatus for inspecting pattern defects according to claim 6, wherein
the light modulating means is equipped with a filter that uses a dielectric film whose transmittance is controlled.

14. A method of inspecting pattern defects, comprising the following steps of:
illuminating a sample on whose surface a pattern was formed by light emitted from illumination means;
forming an optical image of the pattern of the illuminated sample with an imaging optical system;
detecting an image of the pattern of the sample by detecting the formed optical image; and
detecting pattern defects on the sample by processing the detected image; wherein:
the step of illuminating further comprises a step of selecting a combination of a wavelength of light for illuminating the sample, and an aperture diaphragm of the illumination means,
the step of forming an optical image further comprises a step of selecting an aperture diaphragm of the imaging optical system, and
prior to performing the step of detecting a pattern defect, performing the steps of processing the detected image to reduce noise, and reconstructing noise reduced images that have been degraded from the noise reduction process.

15. The method of inspecting pattern defects according to claim 14, wherein
the sample is illuminated by a lamp and a laser.

16. The method of inspecting pattern defects according to claim 14, wherein
the sample is illuminated by a lamp.

17. The method of inspecting pattern defects according to claim 14, wherein
the sample is illuminated by a laser.

18. The apparatus for inspecting pattern defects according to claim 14, wherein
the illumination is performed using a plurality of lights having different wavelengths, intensities of the plurality of illumination lights are measured, and
the intensities of the plurality of illumination lights are adjusted so that a ratio of the measured intensities of the plurality of illumination lights becomes constant.

19. A method of inspecting pattern defects, comprising the following steps of:
illuminating a sample on whose surface a pattern was formed with light emitted from illumination means;
forming an optical image of the pattern of the sample with an imaging optical system;
detecting an image of the pattern of the sample by detecting the formed optical image; and
detecting pattern defects on the sample by processing the detected image;

wherein the step of forming an optical image further comprises a step of controlling the intensity and/or phase of the light, and wherein prior to performing the step of detecting a pattern defect, performing the steps of processing the detected image to reduce noise, and reconstructing noise reduced images that have been degraded from the noise reduction process.

20. The method of inspecting pattern defects according to claim 19, wherein the sample is illuminated using a lamp and a laser.

21. The method of inspecting pattern defects according to claim 19, wherein the sample is illuminated by a lamp.

22. The method of inspecting pattern defects according to claim 19, wherein the sample is illuminated by a laser.

23. The method of inspecting pattern defects according to claim 19, wherein the illumination is done using a plurality of illumination lights having different wavelengths, the intensities of the plurality of illumination lights are measured, and the intensities of the plurality of illumination lights are adjusted so that a ratio of the measured intensities of the plurality illumination lights becomes constant.

* * * * *